United States Patent [19]
Verdura et al.

[11] Patent Number: 6,165,184
[45] Date of Patent: Dec. 26, 2000

[54] SYSTEMS METHODS AND INSTRUMENTS FOR MINIMALLY INVASIVE SURGERY

[75] Inventors: Javier Verdura, Marietta; Maureen E. Carroll, Atlanta, both of Ga.; Richard Beane, Hingham, Mass.; Steven Ek, Bolton, Mass.; Mark P. Callery, Shrewsbury, Mass.

[73] Assignees: Smith & Nephew, Inc., Andover; University of Massachusetts, Boston, both of Mass.

[21] Appl. No.: 08/946,500

[22] Filed: Oct. 7, 1997

Related U.S. Application Data

[63] Continuation-in-part of application No. 08/752,167, Nov. 18, 1996, abandoned.

[51] Int. Cl.$^7$ .................................................. A61B 17/04
[52] U.S. Cl. ............................................................ 606/148
[58] Field of Search ................................... 606/148, 213, 606/232; 604/264

[56] References Cited

U.S. PATENT DOCUMENTS

| | | | |
|---|---|---|---|
| 783,924 | 2/1905 | Boehm | 606/211 |
| 3,616,497 | 11/1971 | Esposito, Jr. | 606/205 |
| 4,950,273 | 8/1990 | Briggs | 606/113 |
| 5,035,695 | 7/1991 | Weber, Jr. et al. | 606/42 |
| 5,079,629 | 1/1992 | Oz | 358/100 |
| 5,147,356 | 9/1992 | Bhatta . | |
| 5,167,644 | 12/1992 | Fischell et al. | 604/264 |
| 5,224,930 | 7/1993 | Spaeth et al. | 604/33 |
| 5,242,427 | 9/1993 | Bilweis | 604/264 |
| 5,250,046 | 10/1993 | Lee | 606/29 |
| 5,279,570 | 1/1994 | Dombrowski et al. | 604/164 |
| 5,290,294 | 3/1994 | Cox et al. | 606/108 |
| 5,304,183 | 4/1994 | Gourlay et al. | 606/142 |
| 5,306,287 | 4/1994 | Becker | 606/205 |

(List continued on next page.)

FOREIGN PATENT DOCUMENTS

| | | |
|---|---|---|
| 0 106 748 | 4/1984 | European Pat. Off. . |
| WO 95/13023 | 5/1995 | WIPO . |
| WO 95/22289 | 8/1995 | WIPO . |
| WO 96/27991 | 9/1996 | WIPO . |

OTHER PUBLICATIONS

Cohen et al., "Surgical Application of Milli–Robots", *Journal of Robotic Systems*, 12(6):401–416, (1995).

Goldsmith, "Future Surger: Minimal Invasion," *Med. News & Perspectives*, 264(21):2723, 1990.

Gorey et al., "Video–assisted Nissen's fundoplication using a hand–acess port", *Min. Invas. Ther. & Allied Technol.*, 5:364–366, (1996).

"Mini surgical camera developed in Israel," *Clinica*, 659:18, 1995.

Sastry et al., "Medical Robotics," Web site page: http://robotics/eecs.berkeley.edu/~lara/medical.html, Jun. 12, 1996.

Schurr et al., "Development of steerable instruments for minimal invasive surgery in modular conception", *Acta chir. belg.*, 93:73–77, (1993).

*Primary Examiner*—Michael Buiz
*Assistant Examiner*—Anthony S. King
*Attorney, Agent, or Firm*—Fish & Richardson P.C.

[57] ABSTRACT

Systems, methods, and miniature instruments are disclosed for minimally invasive surgical procedures. A miniature surgical instrument can be inserted directly into a body cavity through a cannula in a way that a surgeon can insert his or her hand into the cavity through a separate minimal incision and use the miniature instruments. A miniature surgical system can include: a cannula having a hollow body configured to receive a miniature surgical instrument and a tether connected to the instrument; and a plunger sized to engage a proximal end of the body and including a conduit therethrough for receiving the tether. The system can also include the tether and the instrument. During use, the instruments can be quickly and safely removed from the body cavity to enable the surgeon to use his or her fingers, e.g., to manipulate tissue.

18 Claims, 16 Drawing Sheets

U.S. PATENT DOCUMENTS

| | | | |
|---|---|---|---|
| 5,312,423 | 5/1994 | Rosenbluth et al. | 606/148 |
| 5,356,424 | 10/1994 | Buzerak et al. | 606/223 |
| 5,431,665 | 7/1995 | Li | 606/131 |
| 5,441,059 | 8/1995 | Dannan | 128/898 |
| 5,441,486 | 8/1995 | Yoon | 604/167 |
| 5,456,684 | 10/1995 | Schmidt et al. | 606/41 |
| 5,474,057 | 12/1995 | Makower et al. | 600/214 |
| 5,501,698 | 3/1996 | Roth et al. | 606/205 |
| 5,545,178 | 8/1996 | Kensey et al. | 606/213 |
| 5,556,402 | 9/1996 | Xu | 606/147 |
| 5,584,847 | 12/1996 | Duluco et al. | 606/185 |
| 5,630,805 | 5/1997 | Ternamian | 604/274 |
| 5,649,934 | 7/1997 | Smeltzer, III et al. | 606/122 |
| 5,718,717 | 2/1998 | Bonnutti | 606/232 |
| 5,876,379 | 3/1999 | Beauvais et al. | 604/181 |

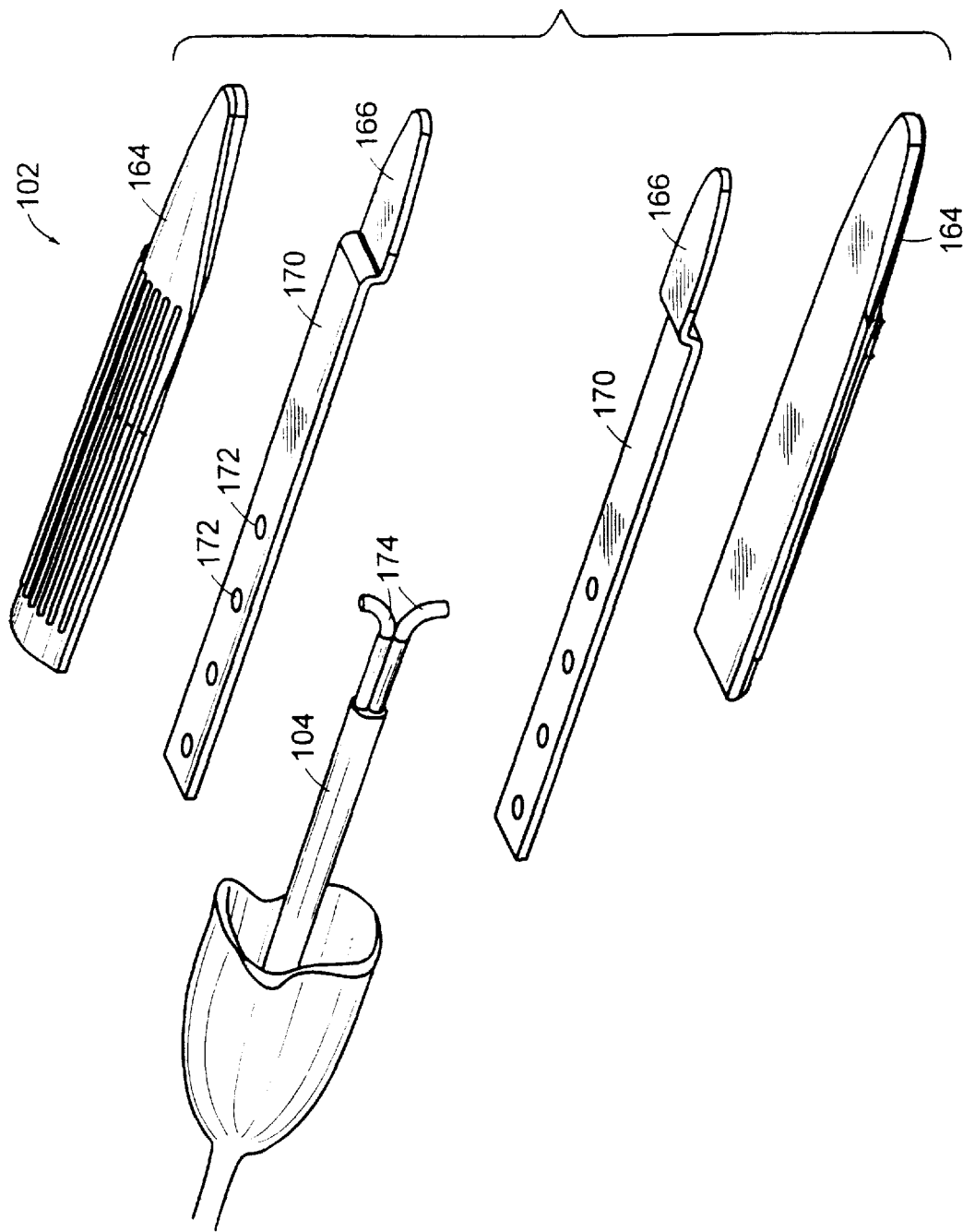

SYSTEMS METHODS AND INSTRUMENTS FOR MINIMALLY INVASIVE SURGERY

CROSS REFERENCE TO RELATED APPLICATIONS

This application is a continuation-in-part of U.S. Ser. No. 08/752,167, filed Nov. 18, 1996, now abandoned.

BACKGROUND OF THE INVENTION

The invention relates to minimally invasive surgical instruments and techniques.

Minimally invasive surgical techniques, including endoscopic (gastrointestinal) and laparoscopic (abdominal) procedures, typically employ surgical instruments that are inserted into the body through a pre-existing orifice or a small puncture or incision rather than the larger incision used in traditional, "open" surgery. Minimally invasive procedures have several advantages over open surgery, the main one being minimization of trauma to healthy tissue. As a result, recovery is accelerated and the risk of complications from infection and scar adhesion is reduced.

Moreover, it has been shown that endoscopic surgery also avoids systemic traumas that occur during open surgery, and it appears that minimization of the size of the incision is not the primary benefit of endoscopic surgery. These systemic traumas include loss of body temperature, tissue desiccation, and other issues related to tissue exposure. These considerations have motivated the application of minimally invasive techniques wherever feasible. However, the instruments used in these minimally invasive procedures can impair or reduce surgical access, dexterity, efficiency, and in some cases safety, when compared to the use of standard instruments in open surgery.

Nearly all minimally invasive procedures employ means for imaging the surgical site in real time. These may be non-invasive, e.g., fluoroscopy, or invasive, using, for example, an optical fiberscope. Such "scopes" can be flexible, like the endoscope, which is employed in the gastrointestinal tract, or, when the operative site is sufficiently accessible, rigid, like the laparoscope, which is used in abdominal surgery. In both endoscopy and laparoscopy, viewing light is delivered to the surgical site by fiber optics, and the surgeon views the site on an external CRT.

Laparoscopic surgery takes place in an approximately 20×20×20 cm workspace inside the patient created by insufflating the abdominal cavity with air or a gas such as carbon dioxide. The laparoscope and laparoscopic instruments are inserted into the body through a 5 to 12 mm diameter cannula inserted through one or more puncture incisions in the abdominal wall. There are many instruments available for use in laparoscopic procedures including biopsy forceps, various types of graspers, scissors, electrocautery devices, staplers, clip appliers, needle holders, and suture loops for ligation.

In spite of the benefits, there are several limitations of the laparoscopic instruments that make laparoscopy more awkward for the surgeon than traditional, open surgery, and the nature of the instruments require a long learning curve for a surgeon to become proficient in their use. Even after learning how to use these instruments properly, surgeons still lack a certain amount of dexterity, which makes some tasks, such as suturing and knot-tying inside the body cavity, difficult.

Based on the known disadvantages, attempts have been made to improve the position, tactile, and force senses perceived by the surgeon using these laparoscopic instruments in minimally invasive procedures. Force feedback assists in suture and knot tensioning and protects against inadvertent laceration of tissue outside of the field of view of the scope. Tactile sensing is useful for manipulating suture material or other objects held with the instruments, localizing small anatomical features such as subsurface blood vessels, and detecting features that are obscured from the video camera.

Efforts at implementing tactile feedback with these instruments have focused on elaborate linkage designs or the use of complex strain sensor arrays on the tip of the instrument coupled to stimulator arrays worn on the surgeon's fingertips, e.g., on a glove, at a point remote from the tip of the instrument. Such systems have had some experimental success, but are complicated, both to design and to manufacture.

SUMMARY OF THE INVENTION

The invention is based on the discovery that miniature surgical instruments can be inserted directly into a body cavity through a valved or self-sealing trocar or cannula in a way that the surgeon can insert his or her hand into the cavity through a separate minimal incision, retrieve the instrument from the cannula, and then manipulate and actuate the instrument to perform surgical procedures, all within the body cavity.

Multiple instruments can be sequentially inserted into and removed from the body cavity as needed by the surgeon, all without requiring the surgeon to remove and reinsert his or her hand through the incision, thus reducing the loss of pressure in the cavity, and reducing the tissue trauma caused by such repeated hand movements.

The instruments can be quickly and safely removed from the body cavity by means of, e.g., a tether attached to one end of the instruments, to allow the surgeon to use his or her fingers freely, e.g., to manipulate tissues, without any encumbrance.

A miniature surgical system facilitates the exchange of instruments into and out of the body cavity. The system includes a cannula having a hollow body configured to receive an instrument, a tether connected to the instrument, and a plunger that has a conduit for receiving the tether and engages a proximal end of the cannula.

During use, the cannula is inserted in an opening into the cavity. Muscles surrounding the opening tighten around the cannula and secure the cannula to the body. Once secured, the cannula provides a passage into the cavity though its hollow body. The tether is passed through the conduit in the plunger and pulled tight so that the instrument and plunger are adjacent one another. The instrument and plunger are then inserted into the passage provided by the cannula so that instrument rests within the body and the plunger engages the proximal end of the cannula, i.e., the end outside the cavity. The system includes air-tight seals between the plunger and the cannula and between the tether and the plunger to prevent any loss of insufflation pressure. In this configuration, the instrument can be drawn into the cavity by pulling the instrument from the cannula from within the cavity and subsequently the instrument can be drawn back into the cannula by pulling on the tether from outside the cavity.

In general, in one aspect, the invention features a miniature surgical cannula system that includes: a cannula including a hollow body configured to receive a miniature surgical instrument and a tether connected to the instrument; and a plunger sized to engage a proximal end of the hollow cannula body and including a conduit therethrough for receiving the tether. It is generally preferred that the conduit communicates with an interior of the hollow cannula body when the plunger engages the proximal end of the hollow cannula body.

The system can also include a sealing ring contacting an interior surface of the body and an outer surface of the plunger to provide an air-tight seal between the plunger and the cannula. The sealing ring can be fixed to the interior surface of the body. The system can also include another sealing ring disposed in the plunger within the conduit to provide an air-tight seal between the plunger and the tether.

The system can also include the tether, which can be an electrical cord. The system can also include the instrument, and the tether can be releasably connected to the instrument.

The hollow cannula body can include a groove or a protrusion on its inner surface, and the plunger can include a corresponding groove or protrusion on its outer surface. The groove and protrusion mate with one another allowing the plunger and cannula to be releasably locked to one another.

The outer surface of the distal end of the cannula body can include helical protrusions for screwing the cannula into an opening into a body cavity. The cannula can also include an insufflation port. The plunger can have a distal tubular portion and an enlarged proximal portion, and the tubular portion can include at least one hole through at least a portion of its thickness.

In general, in another aspect, the invention features a surgical cannula sealing system that includes: a tether for connecting to a miniature surgical instrument; and a plunger that fits into and seals the cannula having a conduit therethrough sized to receive the tether. For example, the tether can be an electrical cord.

The system can also include a sealing ring located between an inner surface of the plunger adjacent the conduit and an outer surface of the tether to provide an air-tight seal between the plunger and the tether. The system can also include the instrument, and the tether and instrument can be releasably connected to one another.

The plunger can have a distal tubular portion and an enlarged proximal portion. The plunger can also be sized to be partially received within a hollow body of a cannula.

In another aspect, the invention features a surgical instrument exchange cannula including a hollow, cylindrical body configured to receive a miniature surgical instrument, a first valve, e.g., a split seal valve, located at a distal end of the body, and a second valve located at a proximal end of the body, wherein the first and second valves are operated independently and wherein at least one of the valves is made to contact and seal against a surgical instrument passing through the valve, e.g., made of a flexible material. For example, the second valve can be a flap door valve that is opened to insert a miniature surgical instrument and then closed before the instrument is removed from the cannula body through the first valve. The instrument exchange cannula can further include an attachment point, e.g., an eyelet or hook, for a tether, either inside or outside the hollow body.

The instrument exchange cannula can further include a plunger arranged to pass through an opening in the flap door valve and slide within the body of the cannula, wherein the plunger has a length sufficient to enable a user to push a miniature surgical instrument within the cannula a sufficient distance so that a distal end of the instrument passes through the first valve and protrudes out of the distal end of the cannula body. This plunger arrangement can further include a spring arranged to bias the plunger in an extended, non-depressed position.

In another aspect, the invention further features a method of conducting minimally invasive surgery in a body cavity of a patient by making a primary minimal incision for a hand access port, and arranging the hand access port in the primary incision; inserting a hand into the body cavity through the hand access port; making at least one secondary minimal incision for a miniature surgical instrument exchange cannula, and inserting the instrument exchange cannula into the secondary incision; inserting a first miniature surgical instrument through the instrument exchange cannula into the body cavity; and manipulating and/or actuating the surgical instrument with the hand within the body cavity to perform minimally invasive surgery. These steps can be performed in any order required for a particular case. For example, the hand can be inserted into the body cavity after the secondary incision is made.

It is generally preferred that the body cavity is insufflated during minimally invasive surgery, and the new methods enable the surgeon to maintain pneumoperitoneum throughout the procedure. The method can further include a step of removing the first miniature surgical instrument from the body cavity and inserting a second miniature surgical instrument through the instrument exchange cannula. This further step can be performed without removing the hand from the body cavity. Certain surgical instruments can be manipulated by hand within the body cavity and actuated from outside the body cavity. The miniature surgical instrument can be, for example, a grasper, scissors, needle holder, clip applier, dissector, resector, scalpel, electrocautery scalpel, or gauze pad. The method can also include a step of temporarily storing the miniature surgical instrument within the instrument exchange cannula, and then removing the instrument from the cannula and using the instrument again, all without removing the hand from the body cavity.

In another embodiment, the invention features a minimally invasive surgery system including a surgical instrument exchange cannula, a hand access port, and at least one miniature surgical instrument.

Furthermore, in another aspect, the invention features a minimally invasive, miniature surgical instrument that includes an elongate body having distal and proximal ends, a surgical tool connected to the distal end of the body, and a retrieval component connected to the proximal end of the body, wherein the instrument has an overall external diameter of less than 15 mm, i.e., to fit within the surgical instrument exchange cannula. For example, the retrieval component can be designed to receive a tether, e.g., it can be in the form of an eyelet. The instrument can include a tether secured to the retrieval component. In some embodiments, the tether can be an electrical conductor, e.g., where the surgical tool is an electrocautery scalpel or probe.

For example, the miniature surgical instrument can be in the form of surgical scissors, wherein the body includes a pair of rigid arms having distal and proximal ends, wherein the arms are connected at their proximal ends, and wherein the surgical tool includes a pair of cutting blades each rigidly secured to a distal end of one of the arms. The retrieval component can be an eyelet or hook to which a tether can be attached.

In another embodiment, the instrument can be in the form of a surgical grasper, wherein the body includes a pair of rigid arms having distal and proximal ends, wherein the arms are connected at their proximal ends, and wherein the surgical tool includes a pair of grasping tips each rigidly secured to a distal end of one of the arms. Again, the retrieval component can be an eyelet or hook to which a tether can be attached.

Alternatively, the surgical tool of the instrument can be a scalpel blade, in which case the body includes a hollow opening designed to receive the scalpel blade, and an actuator mechanism arranged to move the scalpel blade into and out of the hollow opening in the body to cause the scalpel blade to move between a protruding, deployed position and a retracted, closed position. This mechanism can be, for example, a rack and a gear turned by a thumbwheel.

In another embodiment, the surgical tool is an electrocautery instrument having a substantially parallel pair of arms connected to the body, with at least one arm having an insulating overmold surrounding a metal shim and an inner surface exposing a conducting surface of the shim. The shim is configured to be connected to an electrical cord, which can be included with the instrument and connected to the retrieval component. The shim can include a substantially planar proximal portion, a substantially planar distal portion having the conducting surface, and a bent portion connecting together the proximal and distal portions. The overmold can project through at least one hole in the shim to anchor the shim within the overmold. The conducting surface can also have serrations. The instrument can also include a second shim and a second conducting surface on the other arm to form a bipolar electrocautery instrument.

In a further embodiment, the instrument includes an actuating component disposed substantially near the proximal end of the body. A portion of the actuating component is movable relative to the body and contacts the tool. For example, the actuating component includes a flexible hollow bulb that surrounds the longitudinal axis of the elongate body and connects to the body at its proximal end, and a movable ring sized to an intermediate diameter of the tool connected to the distal end of the bulb. The tool includes a pair of substantially parallel arms with at least one of the arms having an outer diameter that increases smoothly to a maximum located at an intermediate or distal portion of the one arm. When the bulb is compressed substantially perpendicular to the arms, it pushes the ring along an outer surface of the one arm toward the maximum diameter, thereby forcing the arms together. The bulb can have a number of slits functioning as living hinges and can be made from a resilient, plastic material. The instruments are typically between about 2 and 6 inches long.

The invention also features a new minimally invasive surgical instrument that includes an elongate shaft that includes a flexible section, at least at its distal end, a surgical tool, e.g., a grasper, needle holder, or scissors, connected to the distal end of the shaft, a gripping surface located adjacent the surgical tool and between the tool and the flexible section of the shaft, an actuator handle located at a proximal end of the shaft, and an actuator, e.g., a cable or flexible rod, passing through the shaft and arranged to transmit actuating forces from the actuator handle to the surgical tool.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides several advantages. For example, the cannula in the miniature surgical system can be securely positioned within an opening to a body cavity and is sized to receive any one of a number of miniature surgical instruments. In the embodiment in which the tether passes through the plunger, the smooth fit between an inner diameter of the cannula and an outer diameter plunger allows for an air-tight seal. Furthermore, the smooth fit between the tether and the conduit in the plunger allows for a second strong air-tight seal. These seals prevent the escape of insufflation gases during surgery. The fit between the tether and the channel in the plunger also supports the weight of the instrument, while allowing an instrument connected to the tether to be pulled from within the body cavity and allowing the tether to be pulled from outside the body, thereby drawing the instrument into the cannula.

The plunger can also be releasably locked to the cannula. Furthermore, the plunger, tether, and instrument can be easily removed from the cannula, so that the instrument can be exchanged. The cannula can also be used to receive a trocar used to puncture an opening into the body cavity.

In addition, the new methods and instruments enable a surgeon to perform hand-assisted minimally invasive surgery with tactile feedback that is typically lost when using known minimally invasive laparoscopic or endoscopic surgical instruments. Standard minimally invasive surgery instruments have one or more mechanical linkages that separate the surgeon's hand from the tool, e.g., resector, at the distal (patient) end of the instrument by a long tube and a handle. The compression and elongation of materials used in instruments in this configuration prevent a linear relationship between the surgeon's hand movements and the tool's movements. This, in turn, causes positional uncertainty, disrupts the surgeon's tactile sense of how much pressure is being exerted by the tool, and impairs the surgeon's ability to perform dissections or delicate resections of tissue.

Another advantage of the invention is that the tiny surgical instruments are interchangeably inserted into the body cavity through the cannula in a way that allows the surgeon instant access to the instruments inside the body cavity without the need for repeated insertion and removal of the surgeon's hand through the incision, either to remove the instruments to allow the surgeon to manipulate tissues with his fingers or to exchange instruments. Avoiding repeated insertions of the surgeon's hand causes less trauma to the patient, shortens the surgical procedure, reduces risk of infection, and prevents the escape of insufflation gas from the patient's cavity, thus maintaining pneumoperitoneum.

In addition, the instruments are designed so that they can be quickly and safely removed from the body cavity by means of, e.g., a tether secured to instrument, or by other retrieval means, such as a sliding or helical retrieval mechanism inside the cannula. Moreover, the instruments are designed so that when they are pulled through the body cavity and the cannula they are in a closed or inoperative position to avoid inadvertent damage to tissues within the cavity, or to the inside of the cannula. Further, the new instruments are simple in design, can be easily manufactured, and can be manufactured to be disposable or sterilizable and reusable, as desired.

The electrocautery instrument includes an overmold that limits the conducting surfaces to surfaces on the insides of a pair of arms. Thus, a surgeon can touch the tips and outer surfaces of the instrument without being shocked.

The miniature surgical instrument generally includes a surgical tool connected to the distal end of the instrument's body. In some embodiments, a surgeon handles the instrument at and actuates the tool from the proximal end of the instrument. As a result, using the instrument does not obstruct the surgeon's view of the surgical field. Such instruments include an actuating mechanism at the proximal end of the instrument's body. In one of the embodiments, the actuating mechanism can be compressed perpendicular to the motion it imparts to the tool, making the instrument easier to use in limited surgical spaces.

Other features and advantages of the invention will be apparent from the following detailed description, and from the claims.

BRIEF DESCRIPTION OF THE DRAWINGS

FIG. 18 is an exploded view of the electrocautery instrument of FIG. 11.

DETAILED DESCRIPTION

The miniature surgical instruments and methods of the invention enable a surgeon to perform hand-assisted surgical procedures with his or her hand inside a patient's body cavity with all the benefits of minimally invasive surgery, but with the tactile feedback, control, and ease of manipulation of traditional, open surgery. In addition, the new methods allow for easy exchange of a variety of miniature surgical instruments without removing the hand.

The instruments allow the surgeon to maintain tactile feedback because they are manipulated in much the same way as traditional instruments. However, the new instruments are specially designed to provide better access to target tissues as they are small enough to be manipulated and actuated completely within the body cavity. Further, unlike traditional endoscopic instruments, their use is not limited by elongated shafts restricted by operative portals. In addition, the instruments can be removed from the cavity quickly and easily, e.g., by an attached tether, which allows the surgeon to use his or her fingertips, e.g., to manipulate tissues, totally unencumbered and at any time.

Methods of Use

The miniature instruments a re best used in hand-assisted minimally invasive surgical procedures within the abdomen o r pelvis, such as are currently performed by laparoscopic surgery. Other sites within the body can be accessed as well.

In a minimally invasive setting, i.e., after the body cavity is insufflated (with a standard insufflator), e.g., through a Verress needle, the surgeon performs a visual diagnosis of the inside of the body cavity using standard laparoscopic techniques through a small incision. A standard laparoscope or other device is used throughout the surgery to enable constant visualization of the interior of the cavity.

Once an accurate diagnosis is made, the surgeon locates and creates a new incision of about 2 to 3 inches in length, depending on the size of his or her hand and wrist, prepares a standard hand access port, and palpates the inside of the patient cavity with his or her hand under visualization through the laparoscope. The hand access port can be, for example, an INTROMIT™ (Medtech Ltd. Dublin, Ireland) port that enables the surgeon to introduce a hand into the body cavity and remove it without loss of pneumoperitoneum. The Pneumo-Dexterity Sleeve™ (Pilling Weck, N.C.) can also be used as the hand access port.

The surgeon then determines the best location to insert a trocar or cannula that enables the exchange of miniature surgical instruments into and out of the cavity, i.e., to be literally "dropped" into the surgeon's hand at the proper location. The order in which the previous steps are performed can be altered to suit a particular case.

Figure 1:
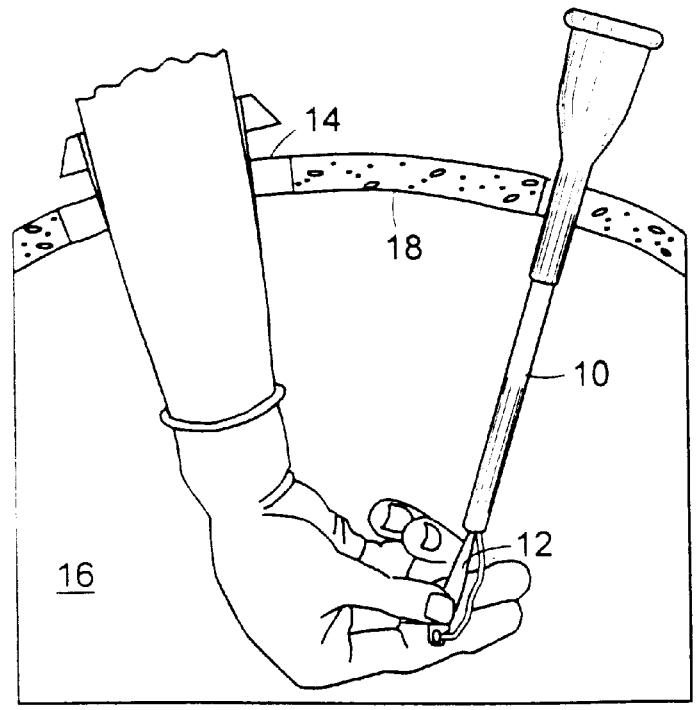
FIG. 1 is a schematic, cross-sectional view of a surgeon's hand and a cannula inserted into a body cavity, showing the surgeon removing a minimally invasive, miniature surgical instrument from the cannula.

As shown in FIG. 1, the surgeon inserts an instrument exchange cannula 10, that can be either a standard trocar such as the ENDOPATH™ TRISTAR™ surgical trocar (Ethicon, Cincinnati, Ohio), or a new instrument exchange cannula described herein, to allow insertion of the miniature surgical instruments (shown generally at 12) into the body cavity 16. The hand access port 14 can be any port that enables the surgeon to introduce a hand into the body cavity 16 and remove it without loss of pneumoperitoneum. This type of hand access port typically consists of a double layer polymer sleeve with a double valve system which is attached to the abdominal wall 18 by a semi-rigid flange.

Once the patient cavity is ready for surgery, the surgeon inserts his or her hand through the hand access port 14. The surgeon then makes full use of his or her hand in manipulating tissues, performing blunt dissection, running bowels, probing for tumors, etc. The instrument exchange cannula is preferably inserted after this procedure, to ensure that it is inserted in the optimal location for access to the miniature surgical instruments by the surgeon.

Figure 2:
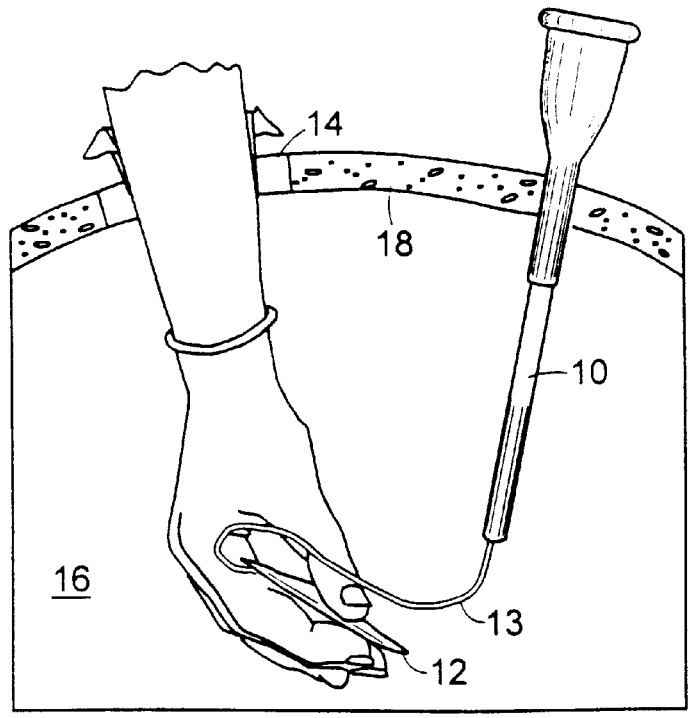
FIG. 2 is a view similar to that shown in FIG. 1, but showing the surgeon deploying the surgical instrument.

Then, as shown in FIGS. 1 and 2, when the need arises for resection, dissection, ligation, etc. by instrument, the surgeon or an assistant inserts an appropriate miniature surgical instrument 12 through the instrument exchange cannula 10, the surgeon removes the instrument from the end of the cannula (FIG. 1), and deploys the instrument (FIG. 2). The instruments 12 can be individually deployed and retracted as needed by means of the tether 13. The instruments are preferably retracted before the surgeon removes his or her hand from the cavity to avoid any inadvertent damage to tissues within the cavity.

Figure 3A:
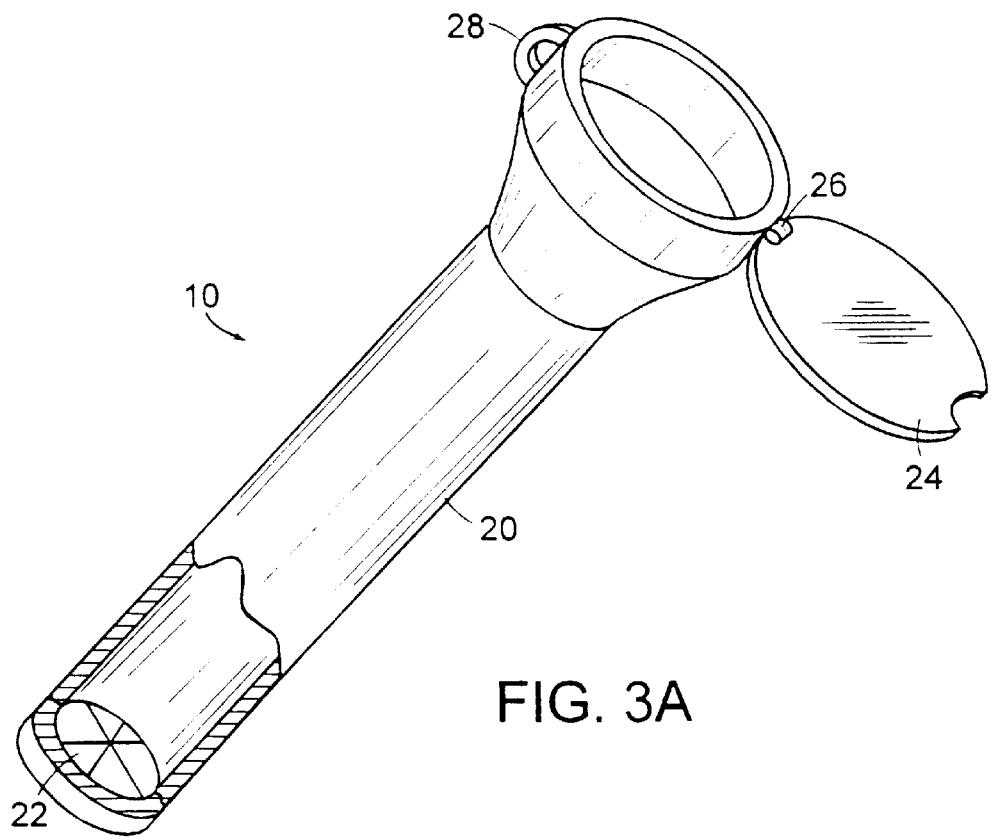
FIG. 3A is a perspective view, in partial cross-section, of a new instrument exchange cannula used to transport miniature surgical instruments into and out of a body cavity.
Figure 3B:
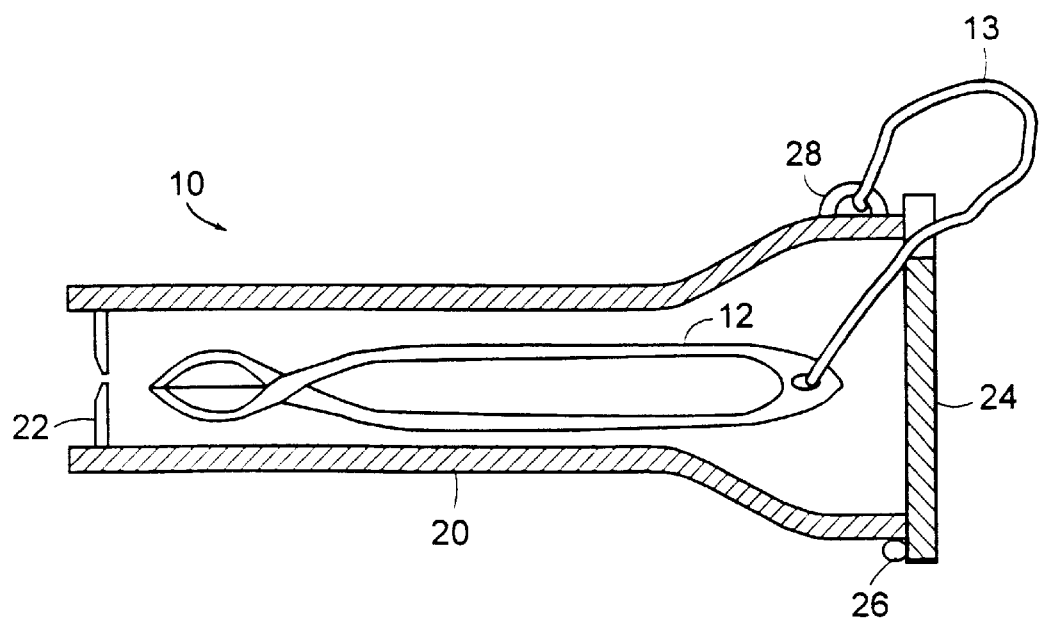
FIG. 3B is a cross-sectional side view of the cannula of FIG. 3A, as used with a miniature surgical instrument and a tether.

New miniature surgical instrument exchange cannulas are shown in FIGS. 3A to 3D. As shown in FIGS. 3A and 3B, the new cannula 10 includes a body 20 having distal and proximal ends. The body is typically made of a medical grade plastic such as polyethersulphones and polyetherimides. The distal end of the cannula body 20 is sealed with a valve 22, such as a split seal valve, which includes a pattern of flaps, e.g., a star pattern, made of a flexible, elastomeric material such as silicone or latex. These elastomeric valves are molded as a single membrane which is then sliced into various patterns. Other valves or seals can also be used, such as flapper seals.

The proximal end of cannula body 20 is sealed with a flap door 24 that is biased in a closed position by a standard torsion spring mechanism 26. The proximal end of cannula body 20 is also provided with a component to which a tether can be attached. In FIGS. 3A and 3B, this component is shown as a closed, circular eyelet 28, but it can also be an open hook to enable easy exchange of tethers. Alternatively, the tethers can include a spring clip at their end to attach to the eyelet 28. The attachment component can also be located on the inner wall of the cannula body 20, e.g., at the proximal end adjacent the flap door 24.

The proximal end of the cannula body 20 can be provided with a flexible gasket, e.g., of silicone, to ensure that an adequate seal is created when the flap door 24 is closed.

FIG. 3B shows the cannula 10 in use with a surgical instrument 12 completely enclosed within the cannula body 20. This mode can be used by the surgeon as a temporary staging area for an instrument while the surgeon uses his or hand to manipulate tissues within the body cavity. Tether 13 connects the instrument 12 to eyelet 28. As shown, when the flap door 24 is closed, tether 13 passes though a pinch point or separate silicone pad in the seal formed around the flap door 24. This enables the tether to be moved into and out of the cannula body, and thus into and out of the body cavity, with the flap door 24 closed and thus, with a minimal loss of pneumoperitoneum.

As shown in FIG. 3B, the length of the cannula body 20 is not much longer than the miniature surgical instrument. In other embodiments, the cannula body can be shorter than the instrument to allow the instrument to extend out of the distal end of the cannula 10 to enable the surgeon to more easily grasp the end of the instrument 12 for use. A short cannula body 20, e.g., shorter than the miniature surgical instruments, also enables the surgeon to insert the instrument into the cannula and push the instrument up to the flap door 24 at the proximal end, where it can be removed without the need for a tether.

Figure 3C:
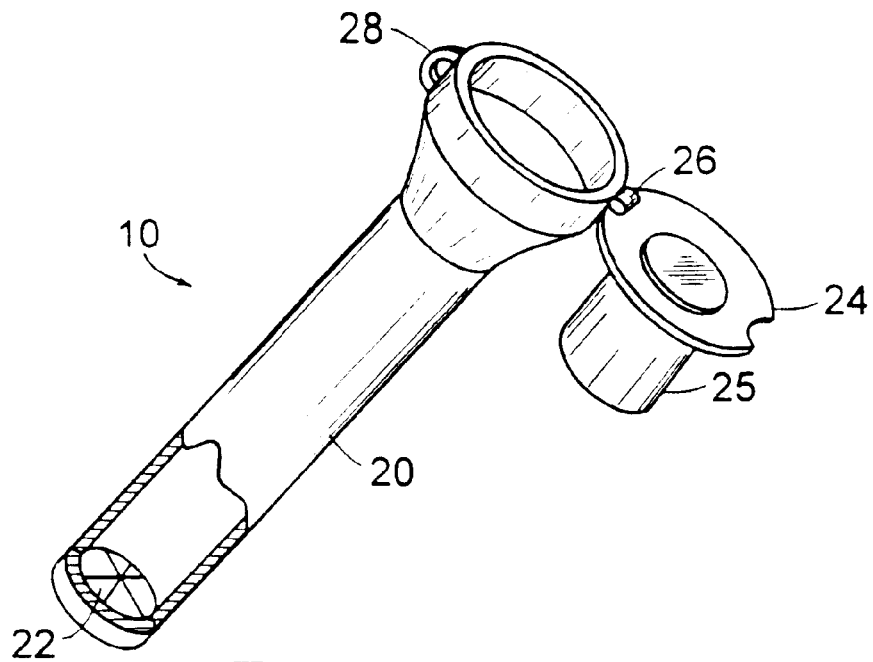
FIG. 3C is a perspective view, in partial cross-section, of another embodiment of a new instrument exchange cannula used to transport miniature surgical instruments into and out of a body cavity.
Figure 3D:
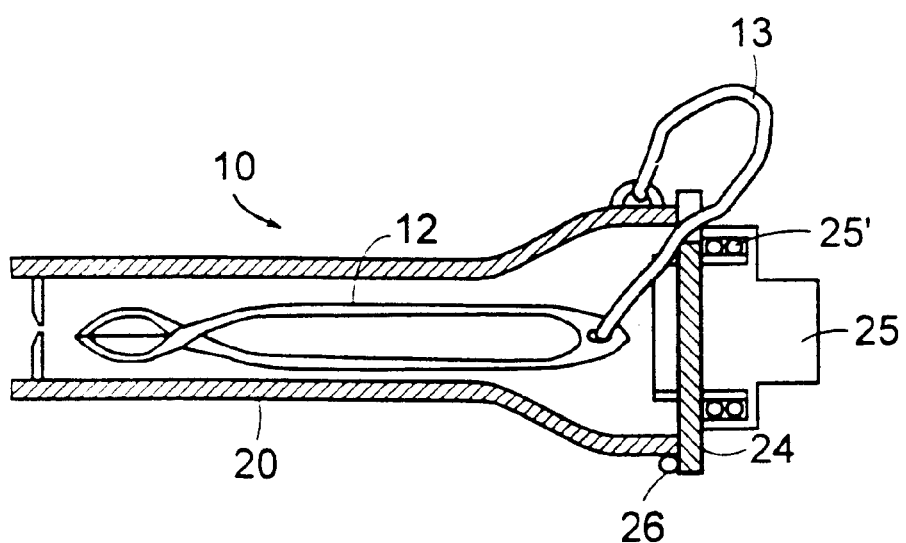
FIG. 3D is a cross-sectional side view of the cannula of FIG. 3C, as used with a miniature surgical instrument and a tether.

FIGS. 3C and 3D illustrate another embodiment of a new surgical instrument exchange cannula 10. In this embodiment, the body 20 and distal end valve 22 are the same as in the cannula shown in FIGS. 3A and 3B, but the flap door 24 is modified to include a plunger 25 that can be used to push the instrument 12 through the body 20 and out through distal end valve 22. This embodiment is preferred when the body of the cannula is longer than the length of the miniature surgical instrument 12.

As shown in FIG. 3D, plunger 25 is mounted through an opening in flap door 24 on a spring 25' that biases the plunger in an extended position. After an instrument 12 is inserted into the body 20 through the proximal end of the cannula, the flap door 24 is closed and sealed, and plunger 25 is depressed or pushed into the body of the cannula, to thereby contact the instrument and push it, or at least a portion of the instrument, out of the distal end of the cannula. The plunger can be connected to the flap door using any standard techniques and known mechanisms to provide a seal between the moving plunger and the door.

Instrument Exchange Cannula and Separate Plunger System

In another embodiment of the exchange cannula, the tether extending from the miniature surgical instrument passes through the plunger. In this case, there is a seal between the tether and the plunger rather than between the tether and a portion of the cannula. There is also a second seal on the interior surface of the cannula that engages the plunger. Together, the first and second seal block the loss of insufflation gases during use of the instrument. In the description that follows, the tether is an electrical cord and the instrument is a bipolar electrocautery instrument. Other instruments and tethers can also be used.

Figure 11:
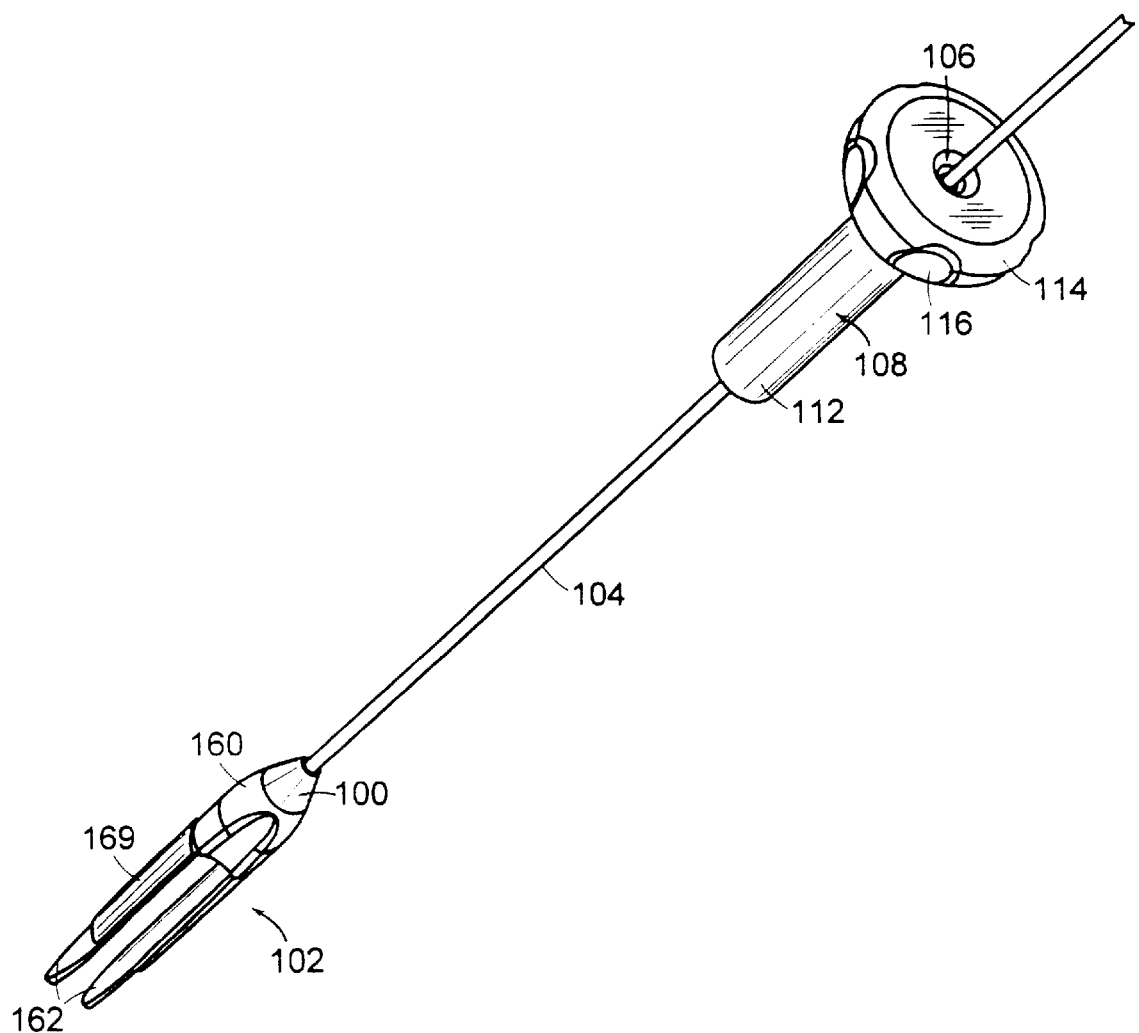
FIG. 11 is a perspective view of a plunger, tether, and an electrocautery instrument.

Referring to FIG. 11, the proximal end 100 of an electrocautery instrument 102 connects to an electrical cord 104 that extends away from instrument 102 and passes through an interior conduit or bore 106 of a plunger 108. A sealing ring 110 (shown in FIG. 15) surrounds a portion of interior bore 106 to provide an air-tight seal between cord 104 and an interior surface of plunger 108. The engagement between sealing ring 110 and cord 104 sufficiently supports the weight of instrument 102, while allowing relative motion between the cord 104 and plunger 108.

Plunger 108 includes a distal tubular portion 112 connected to an enlarged head portion 114. The outer surface of head portion 114 can include dimples 116 so that plunger 108 can be easily grasped. When cord 104 is pulled tight, the region of interior bore 106 surrounded by tubular portion 112 can partially receive the proximal end 100 of instrument 102, which is rounded and tapered.

Figure 12:
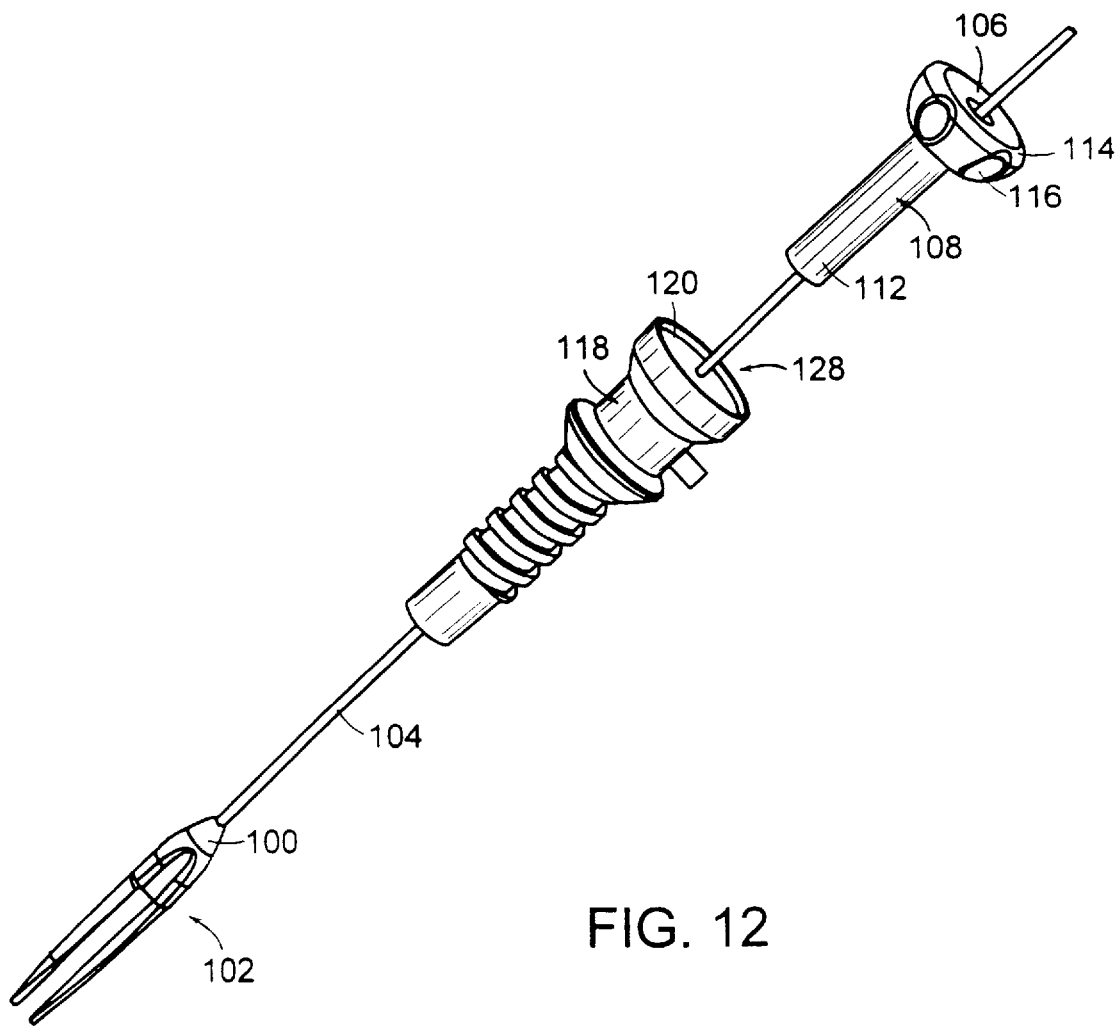
FIG. 12 is a perspective view of the plunger, tether, and instrument of FIG. 11 together with an instrument exchange cannula.

Referring to FIG. 12, instrument 102 and cord 104 can pass through an interior bore 128 of a cannula 118. The proximal end 120 of the cannula can also receive tubular portion 112 of plunger 108 into interior bore 128. Unlike instrument 102, enlarged head portion 114 prevents plunger 108 from passing entirely into or through interior bore 128 of cannula 118. A second sealing ring 122 (shown subsequently in FIGS. 14 and 15) surrounds a portion of interior bore 128 of cannula 118 to provide an air-tight seal between tubular portion 112 of plunger 108 and an interior surface of cannula 118.

Figure 13:
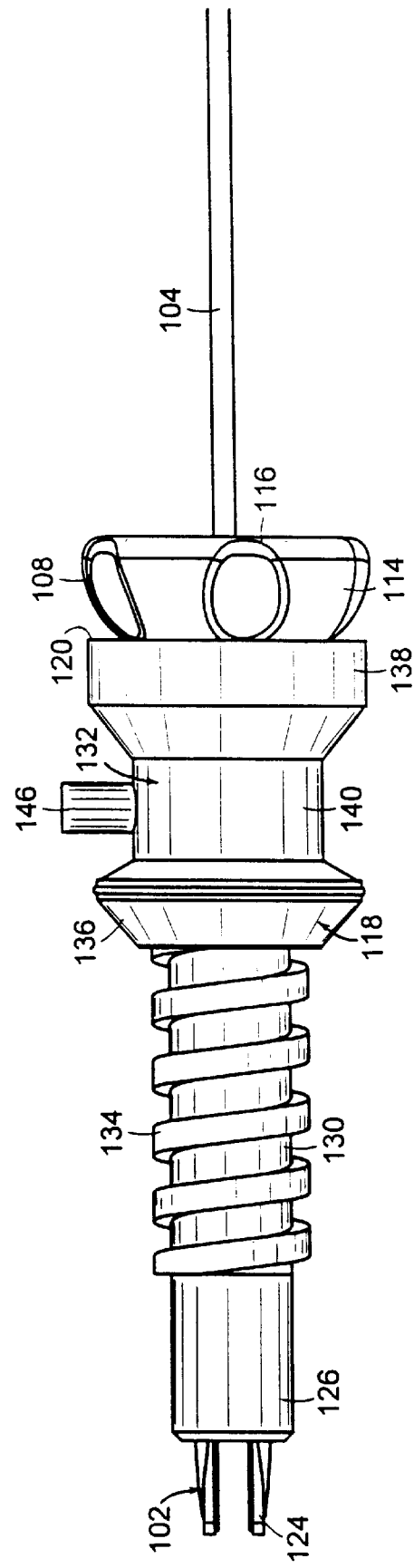
FIG. 13 is a perspective view of the plunger, tether, and instrument of FIG. 11 inserted into the instrument exchange cannula of FIG. 12.

Referring to FIG. 13, plunger 108 and instrument 102, and cannula 118 can be approximated together so that tubular portion 112 and the majority of instrument 102 rest within interior bore 128 of cannula 118. In this approximated state, the distal end 124 of instrument 102 protrudes from the distal end 126 of cannula 118 so that the instrument can be easily grasped during surgery. Cannula 118 includes a distal threaded portion 130 and a proximal hourglass portion 132. Threaded portion 130 includes helical protruding thread 134, which secures cannula 118 to body tissue surrounding an incision. Hourglass portion 132 includes distal and proximal annular portions 136 and 138, respectively, connected by a narrower intermediate portion 140. Distal annular portion 136 in conjunction with threaded portion 130 seal an outer surface of cannula 118 to body tissue surrounding an incision, thereby preventing loss of insufflation gases. Body tissue surrounding the incision tends to enhance this seal. Intermediate portion 140 allows cannula 118 to be easily grasped when inserting instrument 102 and/or tubular portion 112 of plunger 108 into proximal end 120 of cannula 118. The bodies of cannula 118 and plunger 108 are made of medical grade plastic such as polyethersulphones and polyetherimides.

Figure 14:
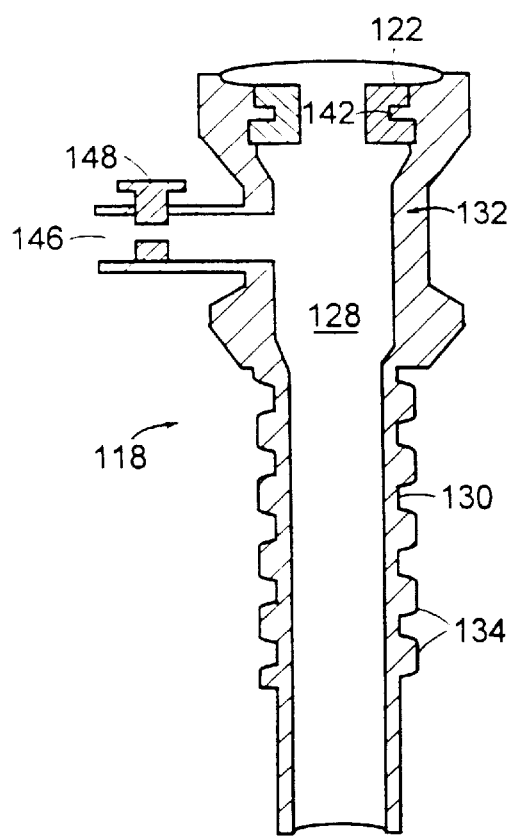
FIG. 14 is a cross-sectional view of the instrument exchange cannula of FIG. 12.
Figure 15:
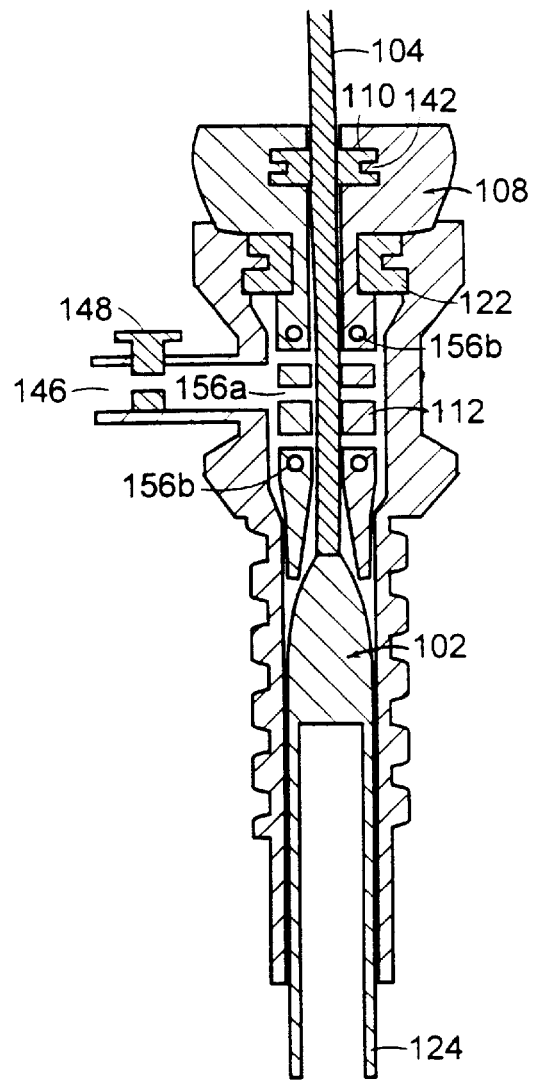
FIG. 15 is a cross-sectional view of the plunger of FIG. 11 received within the instrument exchange cannula of FIG. 12.

Referring to FIGS. 14 and 15, a ridge or tongue 142 secures sealing ring 122 to an interior surface of cannula 118. Ring 122 is a rubber O-ring. Tongue 142 could be replaced by a groove if ring 122 includes a corresponding ridge or tongue. Similarly, a second tongue 144 secures sealing ring 110, which is another rubber O-ring, to an interior surface of plunger 108. In other embodiments, an outer portion of rings 110 and 122 rests in an annular groove within the interior surface of plunger 108 and cannula 118, respectively, rather than fitting over a ridge or tongue.

Alternatively, rather than being O-rings, one or both of sealing rings 110 and 122 can be sheets of elastomeric material (e.g., silastic polymer, thermoplastic rubber, or SANTAPRENE™) having an undersized aperture relative to the diameter of cord 104 or tubular portion 112, respectively. The sheets are secured tightly within the interior surface of plunger 108 or cannula 118, respectively, by annular plates that are screwed together to wedge each of the sheets between them. The elastomeric material will stretch to accommodate objects forced through an undersized aperture.

Cannula 118 also includes an insufflation port 146 containing a valve, such as a standard stopcock valve 148. When plunger 108 is inserted into cannula 118, an insufflator can connect to insufflation port 146 and insufflate a patient's abdominal cavity. Sealing rings 110 and 122 prevent the escape of insufflation gases between either cord 104 and plunger 108 or cannula 118 and plunger 108. In other embodiments, stopcock valve 148 can be replaced with other types of valves, which are well known in the art.

Referring to FIG. 15, tubular portion 112 of plunger 108 includes a plurality of holes 156a, 156b. Holes 156a connect interior bore 106 of plunger 108 to space adjacent the outer surface of plunger 108. Holes 156b connect space on one side of the outer surface to space on another side of the outer surface. During insufflation, holes 156a, 156b decrease the pressure differential between insufflation port 146 and the interior of cannula 118, thereby increasing the inflow capacity of cannula 118.

Figure 16:
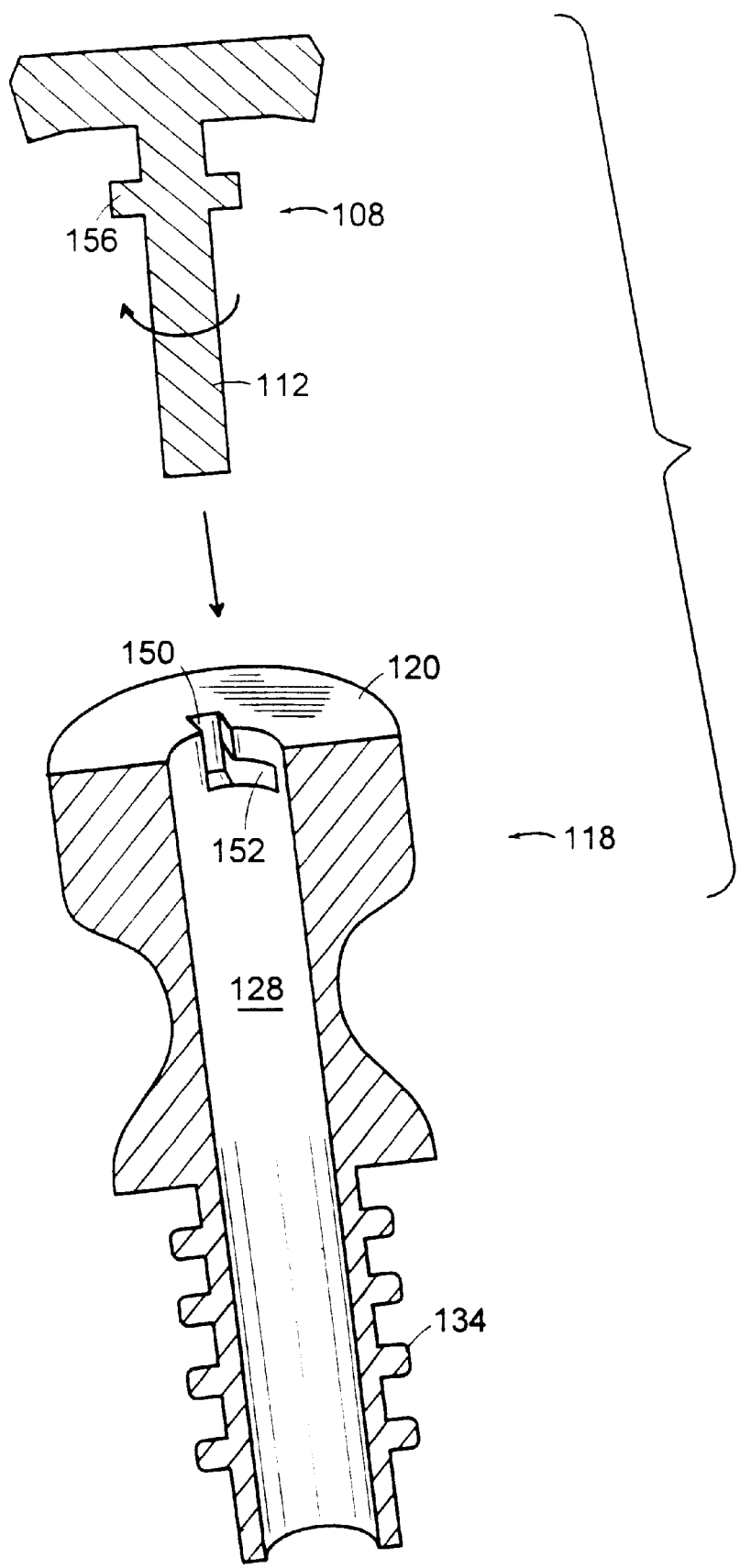
FIG. 16 is a cross-sectional view of a locking mechanism for the plunger and cannula of FIGS. 12–15.

Though not shown in FIGS. 12–15, plunger 108 and cannula 118 can also include a locking mechanism for retaining the tubular portion 112 within the interior of cannula 118 during surgery. Referring to FIG. 16, the interior surface of cannula 118 adjacent its proximal end 120 contains opposite disposed recesses 150 extending into arcuate grooves 152. Tubular portion 112 of plunger 108 includes oppositely disposed protrusions 156 that mate with recesses 150 and arcuate grooves 152. Inserting protrusions 156 into recesses 150 and rotating plunger 108 so that protrusions 156 are within arcuate grooves 152 prevents the relative motion of plunger 108 and cannula 118 along the longitudinal dimension of interior bore 128 of cannula 118. Interior bore 128 of cannula 118 is also sized to receive a standard trocar for puncturing an opening into the abdominal cavity.

After a hand access port has been properly positioned, as described previously, the instrument exchange cannula is used as follows. First, a surgeon makes an incision at a suitable position on a patient's body. Then, a standard trocar is inserted into cannula 118 and proximal end 120 of cannula 118 is wedged into the incision. The trocar is then pushed through cannula 118, puncturing the abdominal wall beneath the incision and making an opening into the abdominal cavity. Once the opening is made, cannula 118 is screwed into the opening using helical threading 134. The trocar is removed, once cannula 118 is securely fastened to the patient's body. Alternatively, a trocar is used separately from cannula 118, and cannula 118 is screwed into the opening after the trocar is removed.

With cannula 118 securely fastened to the body, instrument 102 and plunger 108 are inserted into interior bore 128 of cannula 118 with cord 104 passing through interior bore 106 of plunger 108. Once inside, plunger 108 is rotated within cannula 118 so that protrusions 154 are positioned within arcuate grooves 152 thereby locking together plunger 108 and cannula 118. Valve 148 is then opened and the abdomen is insufflated. Once an appropriate pressure is reached, valve 148 is closed. Alternatively, valve 148 can remain open throughout the procedure, with the insufflator actively maintaining the appropriate pressure.

During surgery, cord 104 can be pulled up from outside the body cavity so that instrument 102 is drawn within cannula 118 and is clear of other surgical procedures within the body cavity. Rounded and tapered distal end 124 of instrument 102 insures that instrument 102 will slide easily into interior bore 128 of cannula 118 upon being drawn up. Sealing ring 110 surrounds cord 104 tightly enough to support the weight of instrument 102 while it is stored within the cannula. When desired, the surgeon can grasp proximal end 100 of instrument 102, which protrudes slightly from cannula 118, and pull it deeper into the abdominal cavity as required. Thereafter, when the surgeon is finished with instrument 102, cord 104 is once again pulled from outside the body to retract instrument 102 into cannula 118. Throughout the procedure, sealing rings 110 and 122 prevent the escape of insufflation gases.

Cord 104 is made of a sturdy, non-resilient material, such as a silastic polymer, which can be adjusted by the surgeon to support the instrument in a desired orientation. This is especially useful if the instrument is a camera and the surgeon is adjusting the camera to enhance viewing.

Instruments can be exchanged during the procedure by unlocking plunger 108 from cannula 118, and removing plunger 108, instrument 102, and cord 104, and thereafter inserting a second plunger, instrument, and cord into cannula 118. After the exchange of instruments, the insufflator is used to reinsufflate the body cavity through insufflation port 146 to compensate for gases lost during the exchange. Alternatively, cannulas can be positioned in multiple openings to make a number of instruments immediately available to the surgeon during a procedure.

Minimally Invasive Surgical Instruments

In general, any surgical tool or tip normally found on traditional surgical instruments can be adapted for use. For example, graspers, scissors, needle holders, clip appliers, dissectors, resectors, scalpels, electrocautery probes and scalpels, gauze pads, and basket punches can be incorporated into the instruments of the invention.

Each instrument includes at least a body and a tool tip, such as a grasper, scalpel, or scissor, at a distal end of the instrument. Many of the instruments also include a retrieval component, at the proximal end of the instrument, e.g., to which a tether or a slider mechanism inside the instrument exchange cannula can be secured. In certain embodiments, the retrieval component can be an eyelet that receives a tether, whereas in other embodiments, the retrieval component is a protruding peg or pin that fits into a slider mechanism or a helical groove inside the cannula.

The tether can be made of a flexible material such as a polymeric filament, or a stainless steel or other ductile, flexible metal, or can be an electrocautery cable. The tether must be rigidly secured to the retrieval component of the miniature surgical instruments to ensure that the tether will not be separated from the instrument upon retraction of the tether through the cannula out of the body cavity. The tether can be secured to the retrieval component at the proximal end of the surgical instrument, such as through an eyelet, or can be rigidly secured to a pin, e.g., by adhesive, or other means. The end of the tether opposite the instrument passes through and out of the cannula to a handle that allows easy grasping of the tether to remove the attached surgical instrument from the body cavity quickly and easily.

All of the instruments also share certain features. For example, they all have a rounded, slim overall profile, and are designed to fit and easily slide within the instrument exchange cannula (as shown in FIGS. 1 and 2). Further, when the retrieval mechanism is a tether, the instrument is preferably designed to allow it to center itself into the cannula when the tether is retracted from the cavity. This design allows the surgeon or assistant to easily remove the instrument from the cavity without the need for the surgeon to manually place the instrument into the cannula.

Alternatively, the surgeon can load the instruments into the cannula as a "temporary holding" area to clear the work area within the body cavity. If the cannula is short, e.g., 2 inches, the surgeon can simply push the instrument into the distal end of the cannula inside the body cavity, and remove it from the proximal end outside the patient. In this case, no tether or other retrieval mechanism is required. In either method, the important concept is that the surgeon can remove the miniature surgical instrument from the instrument exchange cannula, manipulate and actuate the tool with his or her fingers entirely within the cavity, and return the instrument to the cannula with ease.

Other retrieval mechanisms include slider mechanisms or helical groove mechanisms provided inside the instrument exchange cannula. For example, a thin slider mechanism can be attached to a miniature surgical instrument, e.g., to a pin or peg protruding from the distal end of the instrument, and is then used to push the instrument out of the distal end of the cannula. The surgeon then unhooks the instrument from the slider and removes the instrument from the cannula. Once the surgeon is done with the instrument, he or she (or an assistant) pushes the slider back into the cannula, and inserts the instrument into the distal end of the cannula where the pin on the instrument engages into a slot or groove in the slider. Once engaged, the slider is used to pull the instrument out of the cavity through the cannula.

In another embodiment, a helical groove mechanism can also be used. In this embodiment, a hollow tube having an outer diameter slightly less than that of the cannula is inserted into the cannula. This hollow tube has a helical groove cut into its inner surface. When this mechanism is used, the retrieval component of the surgical instrument is a pin or peg that fits into the groove. To remove the instrument from the body cavity, the instrument is inserted into the distal end of the tube so that the pin or peg engages the helical groove. By turning the tube, e.g., with a handle or knob attached to the tube outside the cannula (and the patient), the pin moves slowly up and into the tube along the helical groove, thus moving the instrument into the tube and withdrawing it from the cavity.

The complete miniature surgical instruments are dimensioned to fit into a surgeon's hand, as shown in FIGS. 1 and 2. Thus, in a typical configuration, the instrument is approximately 2 to 4 inches or less in overall length. The overall height or width of the instrument is about 4 to 10 mm in diameter, to fit easily into instrument exchange cannulas having an inner diameter of 5 to 12 mm.

The concepts of the miniature, minimally invasive surgical instruments will now be described in detail with respect to several specific instruments.

Graspers

Figure 4A:
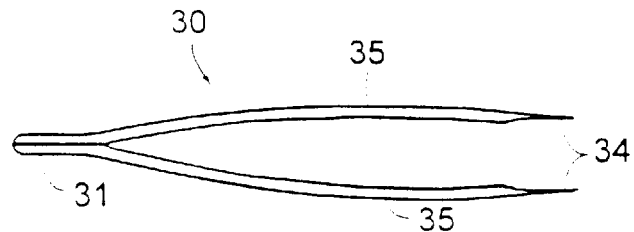
FIG. 4A is a side schematic view of a minimally invasive surgical grasper.
Figure 4B:
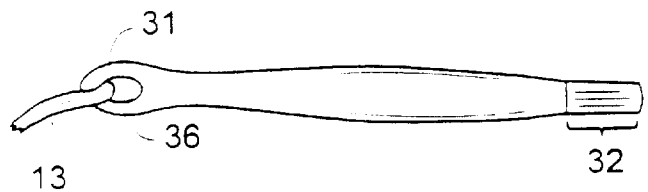
FIG. 4B is a top schematic view of the surgical grasper of FIG. 4A.

FIGS. 4A and 4B show a miniature fine grasper 30 having a proximal end 31 and a grasper end 32, with grasping tips 34. Grasper 30 includes a pair of rigid arms 35 secured to each other at proximal end 31. In this grasper, the retrieval component is an eyelet 36 to attach a tether 13. The arms 35 are attached to each other so that they are spring-biased in an open position. As shown in FIG. 4A, arms 35 are slightly curved, as are grasping tips 34, so that when the arms 35 they are squeezed together, only grasping tips 34 contact each other. This configuration allows for a precise or "fine" manipulation of tissues. The graspers are typically 2 to 4 inches in overall length, and are designed to fit within a 4 to 10 mm diameter.

Wide surface graspers can also be made, in which the grasping surfaces can include gripping teeth or gripping and cutting teeth (not shown). For example, the gripping teeth can be atraumatic and rolled to manipulate with minimal injury those tissues and organs that are intended to be left in place. However, when the grasping surfaces are designed to grip tissues tightly, without regard to injury, e.g., tissues that are to be resected, these teeth can be designed as sharp points to provide greater bite or purchase into those tissues.

For reusable instruments, the graspers are made of robust, autoclavable materials such as surgical stainless steels or titanium. For disposable instruments, the graspers can be manufactured of cast alloys, metal injection-molded alloys, or medical grade plastics such as polyethersulphones and polyetherimides, optionally with metal inserts, e.g., for the grasping tips.

Needle Holder

Figure 5A:
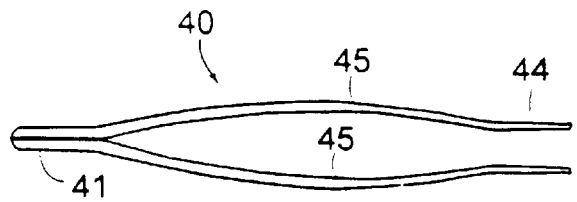
FIG. 5A is a side schematic view of a minimally invasive needle holder.
Figure 5B:
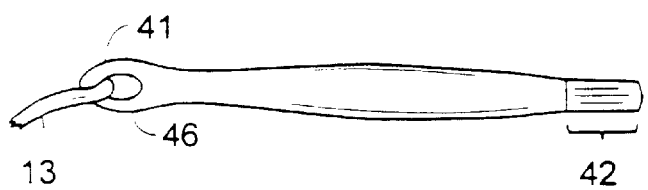
FIG. 5B is a top schematic view of the needle holder of FIG. 5A.

FIGS. 5A and 5B show a miniature needle holder 40 with a proximal end 41, a needle grasping end 42, and a pair of rigid arms 45 secured to each other at the proximal end.

The retrieval component is an eyelet 46, for attachment of tether 13. The arms 45 are attached to each other so that they are spring-biased in an open position. As best shown in FIG. 5A, arms 45 are slightly curved, whereas needle grasping surfaces 44 are flat, so that when arms 45 are squeezed together, the entire flat grasping surfaces 44 contact each other to provide a wide grasping surface to hold a suture needle securely.

The overall dimensions are similar to those of the graspers. As shown in FIG. 5A, the needle holder is also spring-biased in an open position, but may include a locking mechanism, commonly referred to as a ratchet. Such a locking mechanism allows the surgeon to grasp a suture needle and feel the instrument click into a ratcheting, locked position that prevents the jaws of the instrument from opening until the surgeon applies pressure to undo the locking ratchet.

The main difference between the grasper and the needle holder is the nature of the gripping surfaces in the needle holder. These gripping surfaces, e.g., in the form of inserts, must be manufactured of a very hard material such as tungsten carbide steel, and preferably have a textured or knurled surface. These inserts can be of the same material and manufactured in the same way as the gripping surfaces of commercially available needle holders (e.g., those made by Aesculap A. G., Tuttlingen, Germany).

Scissors

Figure 6A:
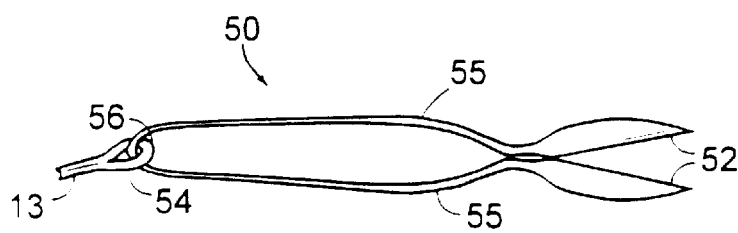
FIG. 6A is a top schematic view of a minimally invasive surgical scissor.
Figure 6B:
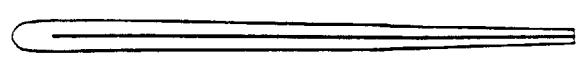
FIG. 6B is a side schematic view of the surgical scissor of FIG. 6A.

FIGS. 6A and B show miniature scissors 50 having a pair of cutting blades 52 and a proximal end 54. Proximal end 54 connects a pair of rigid arms 55 such that the arms and the cutting blades 52 thereto are biased in an open position. Tether 13 is attach through an opening 56 within the proximal end 54 of the scissors, through which tether 13 can be secured. As shown in FIG. 6B, scissors 50 can be manufactured from a single piece of steel or other spring metal, so that cutting blades 52 pass one over the other when arms 55 are pressed towards each other.

The overall dimensions of the scissors are similar to those of the grasper. The main difference between the grasper and the scissors is the cutting blades 52 in the scissors. The blades are designed so that the cutting edges move past each other in a shearing motion, rather than butt against each other in a clamping motion as in the grasper. The cutting edges, e.g., in the form of inserts, of the blades 52, for example if the blades are made of a rigid plastic, must be manufactured of a very hard material such as surgical grade stainless steel or ceramic. These inserts can be of the same material and manufactured in the same way as the blades of commercially available laparoscopic surgical scissors (such as those made by U.S. Surgical Corp., CT).

Scalpel

Figure 7A:
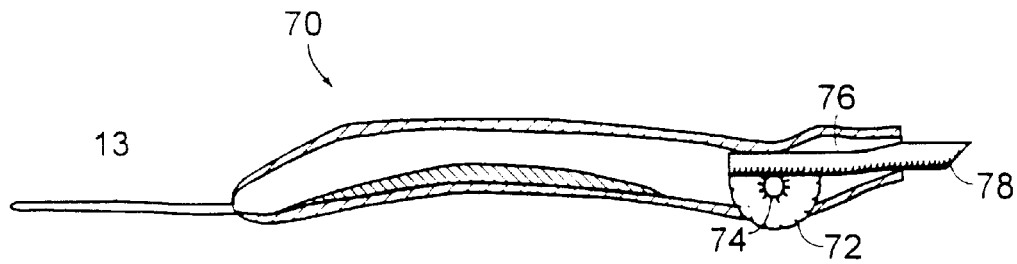
FIG. 7A is a side schematic view of a minimally invasive surgical electrocautery scalpel.
Figure 7B:
FIG. 7B is a top schematic view of the surgical electrocautery scalpel of FIG. 7A.

FIGS. 7A and 7B show a miniature surgical scalpel instrument 70 attached to a tether 13. As shown in FIG. 7A, the scalpel instrument includes a thumb wheel 72 connected to a gear 74 that engages a rack 76 connected to a scalpel blade 78. By turning the thumbwheel 72 the surgeon can accurately control the extent to which the scalpel blade 78 extends from the distal end of the scalpel instrument.

The scalpel blade is typically constructed as a single use blade of a very hard material such as surgical grade stainless steel. The blade is attached to the rack by any standard mechanical means, and is inserted into the scalpel instrument, which can be constructed as a single use device, e.g., of medical grade plastic, or as a reusable device with replaceable single-use blades.

In an alternative embodiment, the scalpel blade is rigidly secured to the miniature surgical instrument, and is covered by a rigid sliding sheath, e.g., of plastic, that can be moved in a proximal direction in a controlled manner to expose the blade.

Electrocauterizing Instruments

Any of the surgical instruments described above, when made of an electrically conducting material, can be adapted to provide an electrocautery feature by adapting the tether to conduct electricity.

Figure 8A:
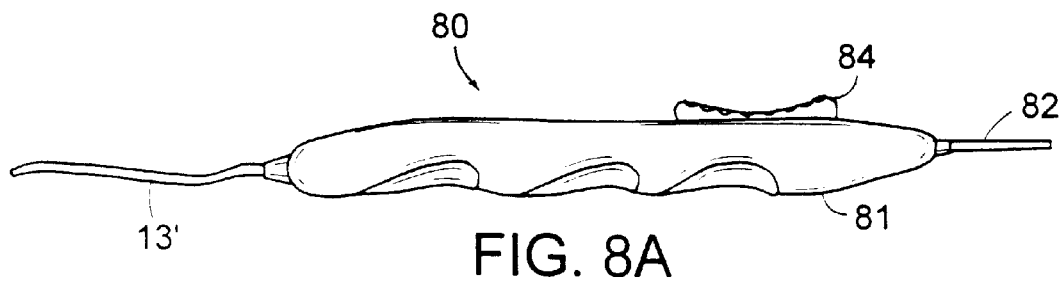
FIG. 8A is a side cross-sectional view of a minimally invasive surgical scalpel.
Figure 8B:
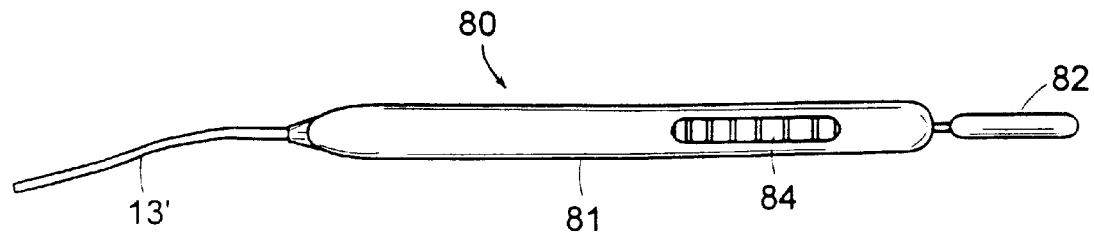
FIG. 8B is a top schematic view of the surgical scalpel of FIG. 8A.

For example, as shown in FIGS. 8A and 8B, a miniature surgical instrument can be configured as an electrocautery scalpel 80. This instrument includes a tether 13' made of a material that conducts electricity covered by an electrical insulator, an electrically insulated body 81, an electrically conducting cutting/cauterizing tip 82, and an electrically isolated, sealed switch 84, which controls the flow of electricity to the tip 82. Switch 84 can be, for example, a toggle switch overmolded and sealed with a silicone cover.

The switch preferably has an off position, a high power (or current) switch position, which enables the surgeon to use the instrument to cut tissue, and a low power switch position, which enables the surgeon to coagulate tissue and blood vessels. This instrument is an example of a monopolar electrocautery device.

As another example, any instrument including two arms or blades can be easily adapted to provide bipolar electrocautery. Such an adaptation requires that the arms which contact the surgeon's hand are insulated, and insulated from each other, by a material such as plastic, or coated with a standard electrosurgical insulation.

To adapt a particular instrument, e.g., the grasper described above, for bipolar electrocautery, arms 35 are electrically insulated except for the grasping tips 34. Furthermore, the tether and eyelet are preferably coated with an insulating material, e.g., a plastic. An electrically conductive tether (insulating on the outside) is attached, e.g., soldered, to the eyelet, and is connected at its other end to a controllable power source.

During bipolar operation, current flows from one grasping tip 34 to the other through the target tissue to be cauterized between the two tips. During monopolar operation, current flows from one tip into the target tissue, and through the patient to a ground. In both embodiments, the majority of the surfaces of the one or two tips are preferably insulated so that the current flow can be controlled.

Figure 17:
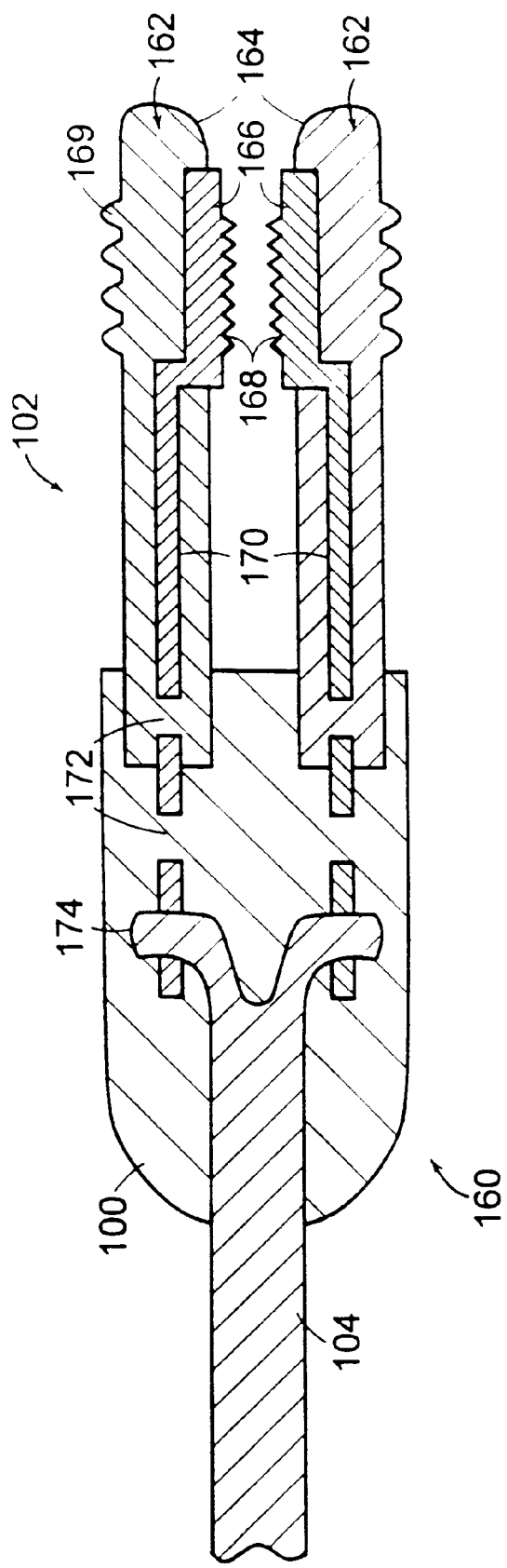
FIG. 17 is a cross-sectional view of the electrocautery instrument of FIG. 11.

Specific bipolar electrocautery instrument will now be described. Referring to FIGS. 11 and 17, an electrocautery instrument 102 is shown. Instrument 102 includes a proximal body portion 160 and a pair of arms 162, each having an insulating outer portion 164 and a conducting inner portion 166. Conducting inner portions 166 protrude from the inner surface of arms 162 and have surface serrations 168 to better grasp tissue to be cauterized. Conducting inner portions 166 also connect to bipolar electrical cord 104. The surfaces 169 of insulating outer portions 164 are textured so that they are easily grasped by a surgeon.

The interior of instrument 102 is shown in FIGS. 17–18. Conducting inner portions 166 are formed from deformed landings at the distal ends of two metal shims 170. The proximal ends of shims 170 have a series of holes 172. A bipolar pair of leads 174 from cord 104 are inserted through a pair of oppositely positioned holes where they are soldered to shims 170. The remainder of arms 162, including insulating outer portions 164, are formed from a thermoplastic such as polypropylene that is molded over and under shims 170, and includes external textured regions to provide the surgeon a secure grip on the instrument. The thermoplastic extends through holes 172 not filled by leads 174, thereby firmly securing shims 170 within arms 162. After molding, the only exposed portions of shims 170 are conducting inner portions 166. Since only the inner portion of arms 162 is conducting, the entire outer length of instrument 102 can be touched safely. Body portion 160 is formed by overmolding proximal ends 176 of shims 170 and proximal ends 178 of arms 162 with additional thermoplastic material. Proximal end 100 of instrument 102 is rounded and tapered to slide easily into an interior bore of a cannula or plunger.

Absorbent Padding

Figure 9:
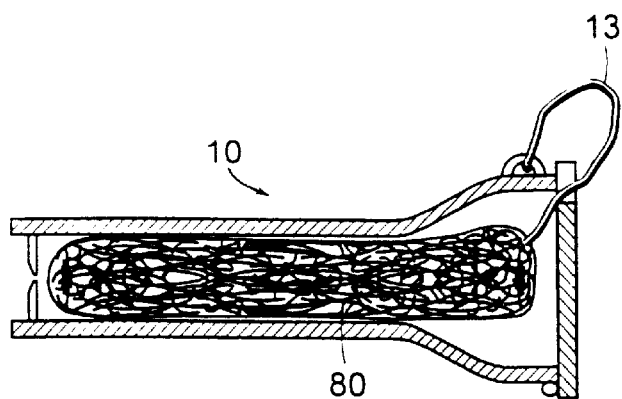
FIG. 9 is a side, cross-sectional view of a new cannula of FIGS. 3A and 3B, in use with a gauze pad and tether.

The miniature surgical instrument can also be a gauze pad, which can be connected to a tether for easy removal from the body cavity. As shown in FIG. 9, the gauze pad 80 is wrapped into a tight, small-diameter cylinder that fits within the instrument exchange cannula 10, and is connected at one end to a tether 13. The surgeon can remove the pad from the cannula if a small portion of the pad extends out of the distal end of the cannula. For example, the pad can be pushed into the body cavity by means of the plunger arrangement shown in FIGS. 3C and 3D.

Although a tether eases removal of the pad from the body cavity, the surgeon can easily insert the pad into the cannula manually for later removal. To ensure that the pad is not lost in the body cavity, it can be manufactured with an X-ray-opaque filament woven into the pad.

Flexible Shaft Instruments

Another type or class of instrument that can be used in conjunction with an instrument exchange cannula, preferably a standard trocar, is a surgical instrument that has a surgical tool located at the distal end of the instrument, which is manipulated by hand within the body cavity, and an actuator handle located at the proximal end, which allows the user to actuate the tool from outside the body cavity.

The surgical tool is connected to the actuator handle by means of a long shaft that is highly flexible for at least part of its length, and that can be inserted into and through the cannula and into the body cavity. This shaft is long enough so that the surgeon can manipulate the tool within the cavity and operate the actuator handle outside the patient. The main requirement for this shaft is that it allows the surgeon to freely manipulate the surgical tool within the body cavity, while simultaneously enabling the surgeon, or an assistant, to actuate the tool by moving the handle located outside of the patient. Thus, the shaft can be rigid in part, e.g., for the section that passes through the instrument exchange cannula, but must include a highly flexible section that enables the surgeon to easily manipulate the tool within the cavity without encumbrance.

The shaft should also include a distal portion, which can be a part of the shaft or a separate part fixed to the shaft, immediately adjacent the tool to provide the surgeon with a sure grip on the shaft. This gripping surface can be created by surface texture, such as knurling, or by a contour, such as a concavity or depression designed to fit the fingertips, or a combination of the two.

Figure 10A:
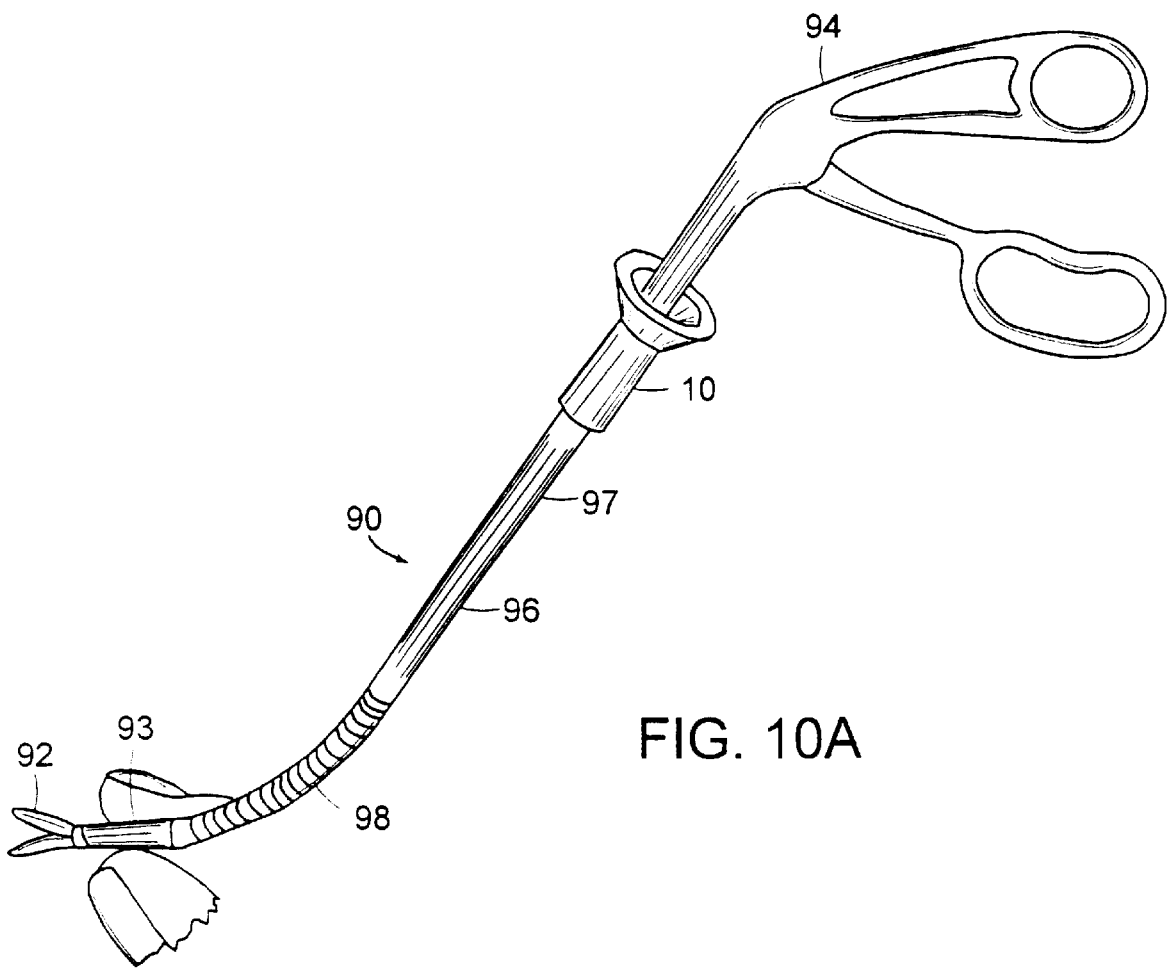
FIG. 10A is a perspective view of a flexible shaft minimally invasive surgical scissors that is inserted into a body cavity through a trocar or cannula, manipulated by hand inside the body cavity, and simultaneously actuated by hand outside the body cavity.

An example of surgical scissors incorporating these concepts is shown in FIG. 10A. Surgical instrument 90 includes a tool in the form of scissors blades 92 at the distal end of the instrument, an actuator handle 94 at the proximal end, and a shaft 96 having both rigid 97 and flexible 98 sections. The distal end of the shaft 96 includes a gripping surface 93 (held by the surgeon's fingertips), which is illustrated in more detail in FIGS. 10B to 10D. In use, the rigid section 97 of shaft 96 passes through the instrument exchange cannula 10, which seals around the shaft to maintain pneumoperitoneum.

Figure 10B:
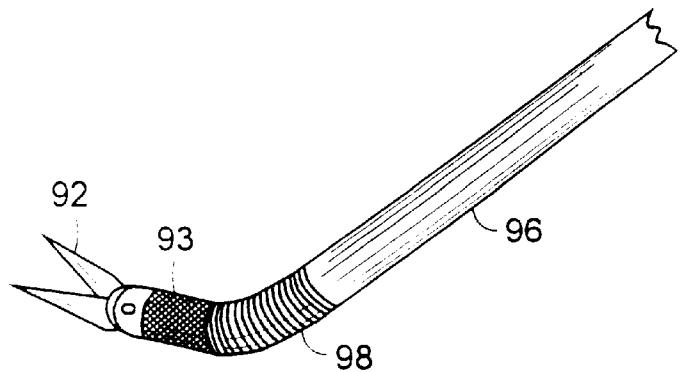
FIGS. 10B to 10D are a series of schematics of different configurations for the distal end of the flexible shaft minimally invasive surgical scissors of FIG. 10A.
Figure 10C:
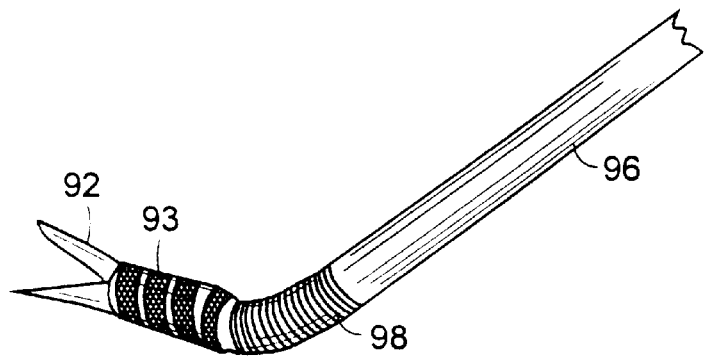
Figure 10D:
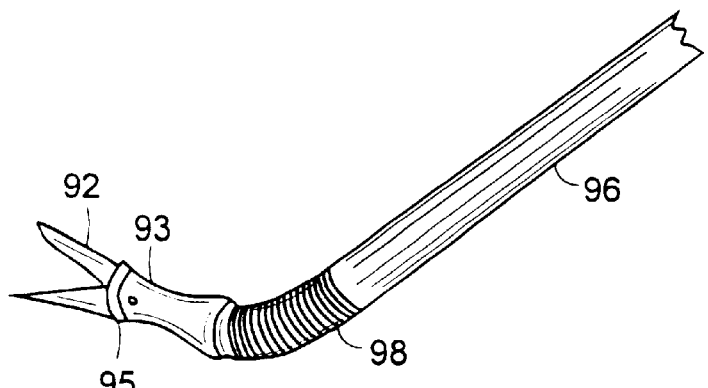

As shown in FIGS. 10B to 10D, the gripping surface 93 can be a knurled surface (10B), a knurled and cut out surface (10C), or a contoured surface that is concave and flared to provide a stop 95 that helps prevent the surgeon's fingers from contacting the scissor blades.

The scissors can be manufactured of surgical grade stainless steel in much the same way as standard laparoscopy scissors. The rigid section of the shaft and the actuator handle are also similar in construction to corresponding parts of typical laparoscopy and endoscopy instruments. The difference between standard laparoscopy or endoscopy instruments and the present surgical instrument is in the highly flexible section at the distal end of the shaft and the gripping surface adjacent the tool. The flexible section must be easily bendable while still accurately transmitting or translating the forces applied to the actuator handle to the scissors blades. This can be accomplished, for example, by means of waffle-cut section molded from a semi-elastic material, or a helical wire coil, which allows flexion of the shaft while maintaining an essentially unchanging length for the inner actuating rod or cable attached to the scissor blades. The key is to maintain a fixed pivot point for the blades while the inner actuator rod or cable can move freely. These parts can be manufactured by standard techniques.

Proximally-Actuated Miniature Surgical Instruments

In some cases a surgeon may prefer to actuate a miniature instrument within the body cavity from its proximal end rather than from its intermediate or distal end. This is to prevent obstructing a view of the operating site adjacent the distal end of the instrument. To facilitate this, proximally-actuated miniature instruments are somewhat longer than those described previously, tending to be about three to six inches in length, but having a comparable diameters. A mechanism for a proximally-actuated instrument will now be described.

Figure 19A:
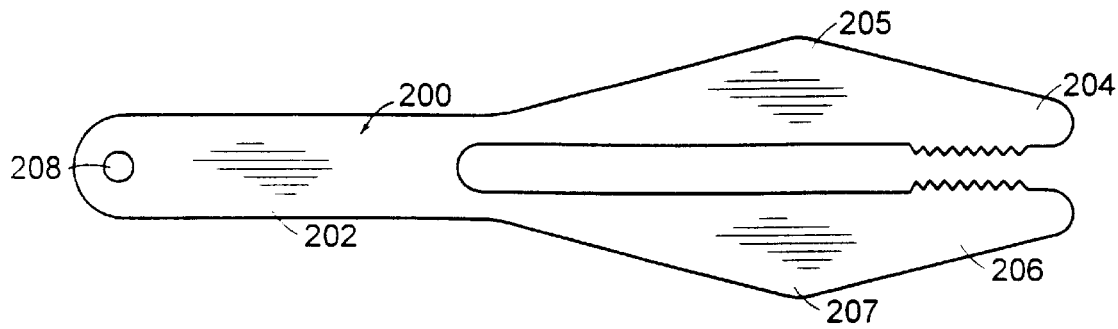
FIG. 19A is a perspective view of a grasper-type instrument.
Figure 19B:
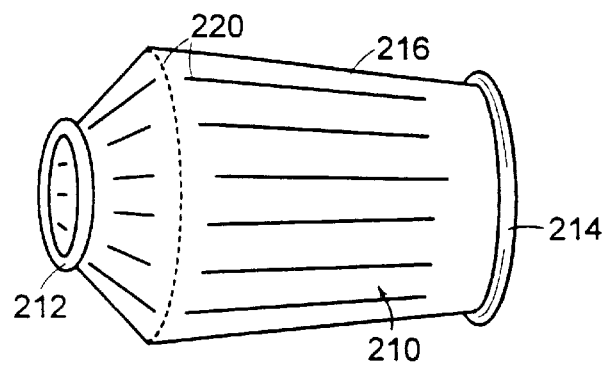
FIG. 19B is a perspective view of an actuating component for use with the grasper-type instrument shown in FIG. 19A.

A grasper-type instrument 200 having a body portion 202 connected to an upper jaw 204 and a lower jaw 206 is shown in FIG. 19A. Instrument 200 is made of medical-grade plastic flexible enough for jaws 204 and 206 to close on one another and grasp tissue. Suitable medical grade plastics include polyethersulphones, polyetherimides, polypropylene, and polyvinyl chloride (PVC). The outer diameters of jaws 204 and 206 gradually increase to a maximum at middle sections 205 and 207 of each jaw, respectively. Body portion 202 has a retrieval component 208, such as a hole or eyelet, that can be connected to a tether. An actuating component 210, shown in FIG. 19B, is sized to slide over body portion 202. Actuating component 210 includes a hollow bulb 216 made from a resilient and semi-flexible molded plastic such as a polyurethane or a SANTAPRENE™ thermoplastic and having a number of slits 220 functioning as living hinges. Bulb 216 connects a proximal ring 212 to a distal ring 214. Rings 212 and 214 are made of either metal, plastic, or plastic molded over metal.

Figure 19C:
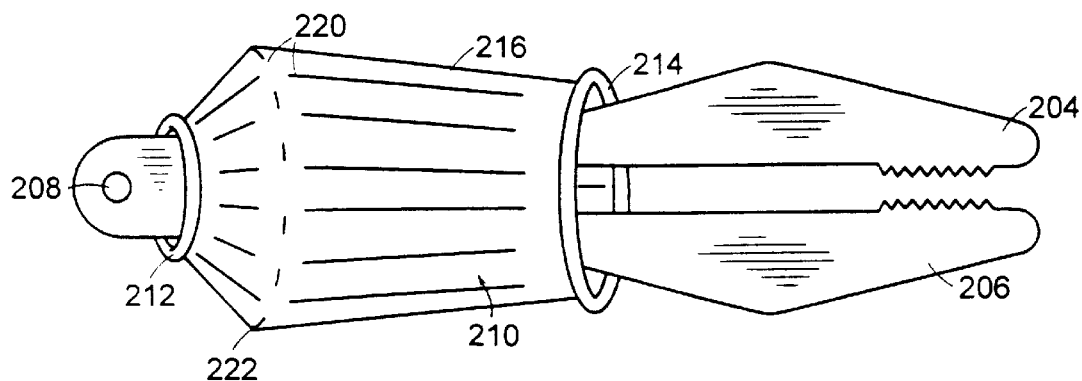
FIG. 19C is a perspective view of a proximally-actuated instrument including the grasper-type instrument shown in FIG. 19A and the actuating component shown in FIG. 19B.

As shown in FIG. 19C, actuating component 210 is slid over body portion 202 of instrument 200 and proximal ring 212 is attached to body portion 202, either by an adhesive or by thermal molding. Alternatively, proximal ring can be fastened to body portion 202 by adhesives, or by other means. Distal ring 214 is free to move.

Figure 19D:
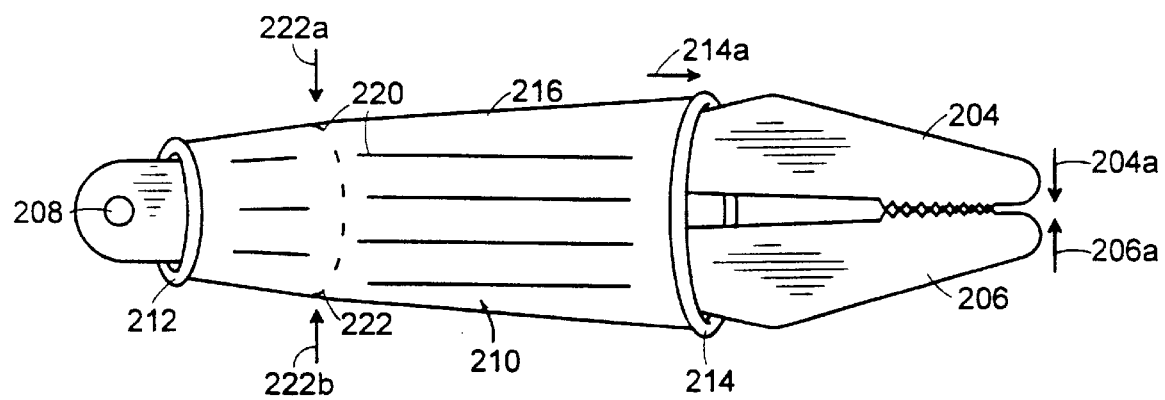
FIG. 19D is a perspective view of the proximally-actuated instrument shown in FIG. 19C when the actuating component is compressed.

The portion 222 of actuating component 210 having the largest diameter includes some of slits 220 along that diameter. These slits function as living hinges such that if portion 222 is compressed (as shown by arrows 222a, 222b), distal ring 214 is pushed towards jaws 204 and 206. The other slits in bulb 216 further facilitate this motion. As shown in FIG. 19D, when distal ring 214 is pushed towards jaws 204 and 206, it forces together jaws 204 and 206 (as shown by arrows 204a and 206a) since distal ring 214 is rigid and the outer diameter of the jaws increases. When portion 222 is released, distal ring 214 slides back to its original position and jaws 204 and 206 are released.

Advantageously, portion 222 can be compressed along any direction substantially perpendicular to the instrument in order to actuate the jaws. This can be especially useful during surgical procedures in which the mobility of a surgeon's hand is limited.

Manufacture of Minimally Invasive Surgical Instruments

The miniature surgical instruments can be constructed using known manufacturing techniques and materials. For reusable instruments, the rigid arms and jaws or grasping ends are preferably machined or stamped from a surgical stainless steel or other metal using standard machine practices.

As an example, the gripping surfaces and teeth described for the grasper can be created by electron discharge machining (EDM). Instruments with tools such as scalpels or scissors that include blades or edges that must be kept extremely sharp, as well as tools used for electrocautery, where the degree of burning or charring would make the instruments difficult to clean, are preferably produced as disposable instruments. These disposable instruments are constructed either of plastics with metal inserts molded or ultrasonically adhered in place, or can also be made entirely of metals, such as stainless steel.

Instruments used as graspers and soft tissue dissectors can be made to be reusable and sterilizable. The sterilizable instruments are preferably constructed of all stainless steel, or of autoclavable plastic with stainless steel tool tips. Alternatively, both the disposable and reusable instruments can be manufactured using metal-injection-molding techniques.

Other Embodiments

It is to be understood that while the invention has been described in conjunction with the detailed description thereof, the foregoing description is intended to illustrate and not limit the scope of the invention, which is defined by the scope of the appended claims.

As another example, a miniature surgical clip applier can be manufactured and used to apply metal or plastic clips to tissues and blood vessels. This instrument has the same general configuration as the graspers described herein, but has a somewhat different jaw configuration designed to apply a crimping force to a clip rather than to grasp or resect tissue. Standard clip applier jaws can be easily adapted to provide a miniature surgical instrument for use with the instrument exchange cannulas described herein. Both a clip applier and a corresponding clip magazine can be inserted into a body cavity through the instrument exchange cannula.

Other aspects, advantages, and modifications are within the scope of the following claims.

What is claimed is:

1. A miniature surgical cannula system comprising:

a cannula comprising a hollow body configured to receive a miniature surgical instrument and a tether connected to the instrument;

a plunger sized to engage a proximal end of the hollow cannula body and comprising a conduit therethrough sized to allow the tether to pass through the plunger and allow relative motion between the tether and the plunger;

a first sealing member contacting an interior surface of the hollow cannula body and an outer surface of the plunger when the plunger engages the cannula to provide an air-tight seal between the plunger and the cannula; and a second sealing member disposed in the plunger within the conduit to provide an air-tight seal between the plunger and the tether when the tether passes through the conduit.

2. The system of claim 1, wherein the conduit communicates with an interior of the hollow cannula body when the plunger engages the proximal end of the hollow cannula body.

3. The system of claim 1,
   wherein the first sealing member is a sealing ring disposed within the hollow cannula body.

4. The system of claim 1,
   wherein the second sealing member is a sealing ring.

5. The system of claim 1, wherein the hollow cannula body comprises one of a groove or a protrusion on an inner surface of the body, and wherein the plunger includes the other of the groove or the protrusion on an outer surface of the plunger, the groove and protrusion configured to mate with one another, thereby locking the plunger within the cannula.

6. The system of claim 5, wherein the groove is on the inner surface of the body and wherein the protrusion is on the outer surface of the plunger.

7. The system of claim 1, wherein the plunger and cannula are configured to be releasably locked to one another.

8. The system of claim 1, wherein an outer surface at a distal end of the cannula body includes helical protrusions for screwing the cannula into an opening into a body cavity.

9. The system of claim 1, wherein the plunger comprises a distal tubular portion and an enlarged proximal portion.

10. The system of claim 9, wherein the tubular portion comprises at least one hole through a wall of the tubular portion.

11. The system of claim 1, further comprising the tether, wherein the tether is sized to slidably pass through the conduit of the plunger and the hollow body of the cannula, and is configured to connect to the instrument.

12. The system of claim 11, wherein the tether is an electrical cord.

13. The system of claim 11, further comprising the instrument, wherein the instrument is connected to the tether and sized to be received by the hollow body of the cannula.

14. The system of claim 13, wherein the tether is releasably connected to the instrument.

15. The system of claim 13, wherein the instrument is manually actuated.

16. The system of claim 1, wherein the cannula includes an insufflation port spaced from the proximal end of the cannula engaged by the plunger.

17. A miniature surgical cannula system comprising:

a miniature surgical instrument selected from the group consisting of, a grasper, scissors, a scalpel, a needle holder, and electrocauterizing instrument;

a tether connected to the manually actuated miniature surgical instrument;

a cannula comprising a hollow body configured to receive the miniature surgical instrument and the tether; and a plunger sized to engage a proximal end of the hollow cannula body and comprising a conduit therethrough sized to allow the tether to pass through the plunger and allow relative motion between the tether and the plunger.

18. A miniature surgical cannula system comprising:

a cannula comprising a hollow body configured to receive a miniature surgical instrument and a tether connected to the instrument; and a plunger sized to engage a proximal end of the hollow cannula body and comprising a conduit therethrough sized to allow the tether to pass through the plunger and allow relative motion between the tether and the plunger, wherein the cannula further comprises an insufflation port spaced from the proximal end of the cannula engaged by the plunger.

* * * * *